(12) United States Patent
Corson et al.

(10) Patent No.: US 6,770,892 B2
(45) Date of Patent: Aug. 3, 2004

(54) METHOD AND SYSTEM FOR AUTOMATED FOCUS-DISTANCE DETERMINATION FOR MOLECULAR ARRAY SCANNERS

(75) Inventors: John F. Corson, Mountain View, CA (US); Stanley P. Woods, Cupertino, CA (US); Russell A. Parker, San Jose, CA (US); Xiangyang Zhou, Mountain View, CA (US); Bo U. Curry, Redwood City, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 50 days.

(21) Appl. No.: 10/086,743

(22) Filed: Feb. 28, 2002

(65) Prior Publication Data

US 2003/0160181 A1 Aug. 28, 2003

(51) Int. Cl.[7] .............................................. G01T 21/64
(52) U.S. Cl. ..................................................... 250/458.1
(58) Field of Search ....................................... 250/458.1

(56) References Cited

U.S. PATENT DOCUMENTS

| | | | |
|---|---|---|---|
| 5,545,901 A | * | 8/1996 | Pentoney et al. ........ 250/458.1 |
| 5,599,695 A | | 2/1997 | Pease et al. |
| 5,721,435 A | | 2/1998 | Troll |
| 5,753,788 A | | 5/1998 | Fodor et al. |
| 5,763,870 A | | 6/1998 | Sadler et al. |
| 5,932,872 A | * | 8/1999 | Price ....................... 250/201.3 |
| 6,130,745 A | * | 10/2000 | Manian et al. .............. 356/123 |
| 6,171,797 B1 | | 1/2001 | Perbost |
| 6,180,351 B1 | | 1/2001 | Cattell |
| 6,207,960 B1 | | 3/2001 | Stern |
| 6,232,072 B1 | | 5/2001 | Fisher |
| 6,242,266 B1 | | 6/2001 | Schleifer et al. |
| 6,323,043 B1 | | 11/2001 | Caren et al. |
| 6,329,143 B1 | | 12/2001 | Stryer et al. |
| 6,371,370 B2 | | 4/2002 | Sadler et al. |
| 6,403,957 B1 | | 6/2002 | Fodor et al. |
| 6,486,457 B1 | | 11/2002 | Dorsel et al. |
| 2002/0061529 A1 | * | 5/2002 | Bridgham et al. ............. 435/6 |
| 2002/0172964 A1 | * | 11/2002 | Ippolito et al. ................ 435/6 |
| 2003/0105195 A1 | * | 6/2003 | Holcomb et al. ........... 524/102 |

* cited by examiner

Primary Examiner—Constantine Hannaher

(57) ABSTRACT

An automated method and system for determining an optimal focus distance for scanning a molecular array scanner. Blocks of rows of a reference array are automatically scanned at successively greater distances of the stage from a light gathering medium, such as an optical fiber, or z-positions, to produce data providing a functional relationship between z-position and measured signal intensities. The data is then processed by a peak-height-based, or window-based, focus-finding routine that selects an optimal focus-distance for data scans.

19 Claims, 21 Drawing Sheets

METHOD AND SYSTEM FOR AUTOMATED FOCUS-DISTANCE DETERMINATION FOR MOLECULAR ARRAY SCANNERS

TECHNICAL FIELD

The present invention relates to the molecular array scanners and, in particular, to automated adjustment of the focal distance at which a sample molecular array is positioned with respect to laser light sources and photodetectors to produce optimal data acquisition.

BACKGROUND OF THE INVENTION

The present invention is related to acquisition of molecular-array data and other types of genetic, biochemical, and chemical data from molecular arrays by molecular array scanners. A general background of molecular-array technology is first provided, in this section, to facilitate discussion of the scanning techniques described in following sections.

Array technologies have gained prominence in biological research and are likely to become important and widely used diagnostic tools in the healthcare industry. Currently, molecular-array techniques are most often used to determine the concentrations of particular nucleic-acid polymers in complex sample solutions. Molecular-array-based analytical techniques are not, however, restricted to analysis of nucleic acid solutions, but may be employed to analyze complex solutions of any type of molecule that can be optically or radiometrically scanned and that can bind with high specificity to complementary molecules synthesized within, or bound to, discrete features on the surface of an array. Because arrays are widely used for analysis of nucleic acid samples, the following background information on arrays is introduced in the context of analysis of nucleic acid solutions following a brief background of nucleic acid chemistry.

Deoxyribonucleic acid ("DNA") and ribonucleic acid ("RNA") are linear polymers, each synthesized from four different types of subunit molecules. The subunit molecules for DNA include: (1) deoxy-adenosine, abbreviated "A," a purine nucleoside; (2) deoxy-thymidine, abbreviated "T," a pyrimidine nucleoside; (3) deoxy-cytosine, abbreviated "C," a pyrimidine nucleoside; and (4) deoxy-guanosine, abbreviated "G," a purine nucleoside. The subunit molecules for RNA include: (1) adenosine, abbreviated "A," a purine nucleoside; (2) uracil, abbreviated "U," a pyrimidine nucleoside; (3) cytosine, abbreviated "C," a pyrimidine nucleoside; and (4) guanosine, abbreviated "G," a purine nucleoside. FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108. When phosphorylated, subunits of DNA and RNA molecules are called "nucleotides" and are linked together through phosphodiester bonds 110–115 to form DNA and RNA polymers. A linear DNA molecule, such as the oligomer shown in FIG. 1, has a 5' end 118 and a 3' end 120. A DNA polymer can be chemically characterized by writing, in sequence from the 5' end to the 3' end, the single letter abbreviations for the nucleotide subunits that together compose the DNA polymer. For example, the oligomer 100 shown in FIG. 1 can be chemically represented as "ATCG." A DNA nucleotide comprises a purine or pyrimidine base (e.g. adenine 122 of the deoxy-adenylate nucleotide 102), a deoxy-ribose sugar (e.g. deoxy-ribose 124 of the deoxy-adenylate nucleotide 102), and a phosphate group (e.g. phosphate 126) that links one nucleotide to another nucleotide in the DNA polymer. In RNA polymers, the nucleotides contain ribose sugars rather than deoxy-ribose sugars. In ribose, a hydroxyl group takes the place of the 2' hydrogen 128 in a DNA nucleotide. RNA polymers contain uridine nucleosides rather than the deoxy-thymidine nucleosides contained in DNA. The pyrimidine base uracil lacks a methyl group (130 in FIG. 1) contained in the pyrimidine base thymine of deoxy-thymidine.

The DNA polymers that contain the organization information for living organisms occur in the nuclei of cells in pairs, forming double-stranded DNA helixes. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to corresponding deoxy-cytidilate subunits of the other strand.

FIGS. 2A–B illustrate the hydrogen bonding between the purine and pyrimidine bases of two anti-parallel DNA strands. FIG. 2A shows hydrogen bonding between adenine and thymine bases of corresponding adenosine and thymidine subunits, and FIG. 2B shows hydrogen bonding between guanine and cytosine bases of corresponding guanosine and cytosine subunits. Note that there are two hydrogen bonds 202 and 203 in the adenine/thymine base pair, and three hydrogen bonds 204–206 in the guanosine/cytosine base pair, as a result of which GC base pairs contribute greater thermodynamic stability to DNA duplexes than AT base pairs. AT and GC base pairs, illustrated in FIGS. 2A–B, are known as Watson-Crick ("WC") base pairs.

Two DNA strands linked together by hydrogen bonds forms the familiar helix structure of a double-stranded DNA helix. FIG. 3 illustrates a short section of a DNA double helix 300 comprising a first strand 302 and a second, anti-parallel strand 304. The ribbon-like strands in FIG. 3 represent the deoxyribose and phosphate backbones of the two anti-parallel strands, with hydrogen-bonding purine and pyrimidine base pairs, such as base pair 306, interconnecting the two strands. Deoxy-guanylate subunits of one strand are generally paired with deoxy-cytidilate subunits from the other strand, and deoxy-thymidilate subunits in one strand are generally paired with deoxy-adenylate subunits from the other strand. However, non-WC base pairings may occur within double-stranded DNA.

Double-stranded DNA may be denatured, or converted into single stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing complementary single-stranded DNA polymers. During renaturing or hybridization, complementary bases of anti-parallel DNA strands form WC base pairs in a cooperative fashion, leading to reannealing of the DNA duplex. Strictly A-T and G-C complementarity between anti-parallel polymers leads to the greatest thermodynamic stability, but partial complementarity including non-WC base pairing may also occur to produce relatively stable associations between partially-complementary polymers. In general, the longer the regions of consecutive WC base pairing between two nucleic acid polymers, the greater the stability of hybridization between the two polymers under renaturing conditions.

The ability to denature and renature double-stranded DNA has led to the development of many extremely powerful and discriminating assay technologies for identifying the presence of DNA and RNA polymers having particular base sequences or containing particular base subsequences within complex mixtures of different nucleic acid polymers, other biopolymers, and inorganic and organic chemical compounds. One such methodology is the array-based hybridization assay. FIGS. 4–7 illustrate the principle of the array-based hybridization assay. An array (402 in FIG. 4) comprises a substrate upon which a regular pattern of features are prepared by various manufacturing processes. The array 402 in FIG. 4, and in subsequent FIGS. 5–7, has a grid-like two-dimensional pattern of square features, such as feature 404 shown in the upper left-hand corner of the array. It should be noted that many molecular arrays contain disk-shaped features, rather than round features. Each feature of the array contains a large number of identical oligonucleotides covalently bound to the surface of the feature. These bound oligonucleotides are known as probes. In general, chemically distinct probes are bound to the different features of an array, so that each feature corresponds to a particular nucleotide sequence. In FIGS. 4–6, the principle of array-based hybridization assays is illustrated with respect to the single feature 404 to which a number of identical probes 405–409 are bound. In practice, each feature of the array contains a high density of such probes but, for the sake of clarity, only a subset of these are shown in FIGS. 4–6.

Once an array has been prepared, the array may be exposed to a sample solution of target DNA or RNA molecules (410–413 in FIG. 4) labeled with fluorophores, chemiluminescent compounds, or radioactive atoms 415–418. Labeled target DNA or RNA hybridizes through base pairing interactions to the complementary probe DNA, synthesized on the surface of the array. FIG. 5 shows a number of such target molecules 502–504 hybridized to complementary probes 505–507, which are in turn bound to the surface of the array 402. Targets, such as labeled DNA molecules 508 and 509, that do not contains nucleotide sequences complementary to any of the probes bound to array surface, do not hybridize to generate stable duplexes and, as a result, tend to remain in solution. The sample solution is then rinsed from the surface of the array, washing away any unbound labeled DNA molecules. Finally, the bound labeled DNA molecules are detected via optical or radiometric scanning. FIG. 6 shows labeled target molecules emitting detectable fluorescence, radiation, or other detectable signal. Optical scanning involves exciting labels of bound labeled DNA molecules with electromagnetic radiation of appropriate frequency and detecting fluorescent emissions from the labels, or detecting light emitted from chemiluminescent labels. When radioisotope labels are employed, radiometric scanning can be used to detect the signal emitted from the hybridized features. Additional types of signals are also possible, including electrical signals generated by electrical properties of bound target molecules, magnetic properties of bound target molecules, and other such physical properties of bound target molecules that can produce a detectable signal. Optical, radiometric, or other types of scanning produce an analog or digital representation of the array as shown in FIG. 7, with features to which labeled target molecules are hybridized similar to 706 optically or digitally differentiated from those features to which no labeled DNA molecules are bound. In other words, the analog or digital representation of a scanned array displays positive signals for features to which labeled DNA molecules are hybridized and displays negative features to which no, or an undetectably small number of, labeled DNA molecules are bound. Features displaying positive signals in the analog or digital representation indicate the presence of DNA molecules with complementary nucleotide sequences in the original sample solution. Moreover, the signal intensity produced by a feature is generally related to the amount of labeled DNA bound to the feature, in turn related to the concentration, in the sample to which the array was exposed, of labeled DNA complementary to the oligonucleotide within the feature.

Array-based hybridization techniques allow extremely complex solutions of DNA molecules to be analyzed in a single experiment. An array may contain from hundreds to tens of thousands of different oligonucleotide probes, allowing for the detection of a subset of complementary sequences from a complex pool of different target DNA or RNA polymers. In order to perform different sets of hybridization analyses, arrays containing different sets of bound oligonucleotides are manufactured by any of a number of complex manufacturing techniques. These techniques generally involve synthesizing the oligonucleotides within corresponding features of the array through a series of complex iterative synthetic steps, or depositing oligonucleotides isolated from biological material.

As pointed out above, array-based assays can involve other types of biopolymers, synthetic polymers, and other types of chemical entities. For example, one might attach protein antibodies to features of the array that would bind to soluble labeled antigens in a sample solution. Many other types of chemical assays may be facilitated by array technologies. For example, polysaccharides, glycoproteins, synthetic copolymers, including block copolymers, biopolymer-like polymers with synthetic or derivitized monomers or monomer linkages, and many other types of chemical or biochemical entities may serve as probe and target molecules for array-based analysis. A fundamental principle upon which arrays are based is that of specific recognition, by probe molecules affixed to the array, of target molecules, whether by sequence-mediated binding affinities, binding affinities based on conformational or topological properties of probe and target molecules, or binding affinities based on spatial distribution of electrical charge on the surfaces of target and probe molecules.

An "array", unless a contrary intention appears, includes any one, two or three dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and the chemical moiety or mixture of moieties at a given feature. "Hybridizing" and "binding", with respect to polynucleotides, are used interchangeably.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 $\mu$m to 1.0 cm. In other embodiments each feature may have a width in the range of 1.0 $\mu$m to 1.0 mm, usually 5.0 $\mu$m to 500 $\mu$m, and more usually 10 $\mu$m to 200 $\mu$m. Non-round features may have area ranges equivalent to that of circular features with the foregoing width (diameter) ranges. At least some, or all, of the features may be of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer of a type of which the features are composed). Such interfeature areas typically will be present where the arrays are formed by processes involving drop deposition of reagents but may not be present when, for example, photolithographic array fabrication processes are used, It will be appreciated though, that the interfeature areas, when present, could be of various sizes and configurations.

The array features can have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m. Features which are not round may have areas equivalent to the area ranges of round features 16 resulting from the foregoing diameter ranges.

Each array may cover an area of less than 100 cm$^2$, or even less than 50, 10 or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Once the labeled target molecule has been hybridized to the probe on the surface, the array may be scanned by an appropriate technique, such as by optical scanning in cases where the labeling molecule is a fluorophore or by radiometric scanning in cases where the signal is generated through a radioactive decay of labeled target. In the case of optical scanning, more than one fluorophore can be excited, with each different wavelength at which an array is scanned producing a different signal. In optical scanning, it is common to describe the signals produced by scanning in terms of the colors of the wavelengths of light employed for the scan. For example, a red signal is produced by scanning the array with light having a wavelength corresponding to that of visible red light.

Scanning of a feature by an optical scanning device or radiometric scanning device generally produces a scanned image comprising a rectilinear grid of pixels, with each pixel having a corresponding signal intensity. These signal intensities are processed by an array-data-processing program that analyzes data scanned from an array to produce experimental or diagnostic results which are stored in a computer-readable medium, transferred to an intercommunicating entity via electronic signals, printed in a human-readable format, or otherwise made available for further use. Molecular array experiments can indicate precise gene-expression responses of organisms to drugs, other chemical and biological substances, environmental factors, and other effects. Molecular array experiments can also be used to diagnose disease, for gene sequencing, and for analytical chemistry. Processing of molecular array data can produce detailed chemical and biological analyses, disease diagnoses, and other information that can be stored in a computer-readable medium, transferred to an intercommunicating entity via electronic signals, printed in a human-readable format, or otherwise made available for further use.

FIG. 8 illustrates components of a molecular array scanner. Lasers 800a–b emit coherent light that passes through electro-optic modulators ("EOMs") 810a–b with attached polarizers 820a–b. Each EOM and corresponding polarizer together act as a variable optical attenuator. A control signal in the form of a variable voltage is applied to each EOM 810a–b by controller 880. The controller 880 may include a suitably programmed processor, logic circuit, firmware, or a combination of software programs, logic circuits, and firmware. The control signal changes the polarization of the laser light, which alters the intensity of the light that passes through the EOM. In general, laser 800a provides coherent light of a different wavelength than that provided by laser 810b. For example, one laser may provide red light and the other laser may provide green light. The beams may be combined along a path toward a stage 800 by the use of full mirror 851 and dichroic mirror 853. The light from the lasers 800a–b is then transmitted through a dichroic beam splitter 854, reflected off fully reflecting mirror 856, and then focused, using optical components in beam focuser 860, onto a molecular array mounted on a holder 800. Fluorescent light, emitted at two different wavelengths (for example, green light and red light) from features of the molecular array in response to illumination by the laser light, is imaged using the optics in the focuser/scanner 860, and is reflected off mirrors 856 and 854. The two different wavelengths are further separated by a dichroic mirror 858 and are passed to photodetectors 850a–b. More optical components (not shown in FIG. 8) may be used between the dichroic mirror and the photodetectors 850a–b, such as lenses, pinholes, filters, and fibers. The photodetectors 850*a–b* may be of various different types, including photo-multiplier tubes, charge-coupled devices, and avalanche photodiodes.

A scan system causes a light spot from each laser 800*a–b* to be moved in a regular pattern about the surface of the molecular array. The molecular array is mounted to a stage that can be moved in horizontal and vertical directions to position light from the lasers onto a particular region at the surface of the molecular array, from which region fluorescent emission is passed back to the photodetectors via the optical path described above. An autofocus detector 870 is provided to sense and correct any offset between different regions of the molecular array and the focal plane of the system during scanning. An autofocus system includes detector 870, processor 880, and a motorized adjuster to move the stage in the direction of arrow 896.

The controller 880 receives signals from photodetectors 850*a–b*, called "channels," corresponding to the intensity of the green and red fluorescent light emitted by probe labels excited by the laser light. The controller 880 also receives a signal from autofocus offset detector 870 in order to control stage adjustment, provides the control signal to the EOMs 810*a–b*, and controls the scan system. Controller 880 may also analyze, store, and output data relating to emitted signals received from detectors 850*a–b*.

The dynamic autofocus mechanism, described above, provides a means for maintaining a constant focus distance during scanning of a molecular array. However, any of various different focus distances may be selected to be held constant during a scan. In general, the focus distance must correspond to the depth of focus of the molecular array optics, but, in general, there is one or a small range of optimal focus distances for a particular molecular array scanner. Designers, manufacturers, and users of molecular arrays have recognized a need for an automated focus-distance optimization method.

SUMMARY OF THE INVENTION

One embodiment of the present invention provides an automated method for determining an optimal focus distance for scanning a molecular array by a molecular array scanner. Blocks of rows of a reference array are automatically scanned over a range of focus distances, or z-positions, to produce data providing a functional relationship between focus distance, or z-position, and measured signal intensities. The data is then processed by a peak-height-based, or local variation-based, focus-finding routine that selects an optimal focus distance for data scans.

The present invention further provides a computer program product for use with an apparatus such as described herein. The program product includes a computer readable storage medium having a computer program stored thereon and which, when loaded into a programmable processor, provides instructions to the processor of that apparatus such that it will execute the procedures required of it to perform a method of the present invention.

DETAILED DESCRIPTION OF THE INVENTION

One embodiment of the present invention is a method for determining an optimal focus distance at which to scan the surface of a molecular array during data collection from the molecular array by an automated molecular array scanner. The molecular array scanner includes dynamic autofocus functionality for maintaining the focus distance at a constant value during scanning of a molecular array. However, current scanners lack an automated focus-distance optimizing feature, and instead require a tedious and error-prone manual optimal focus-distance determination. The method for automated focus-distance determination that represents one embodiment of the present invention may be incorporated into logic circuits, firmware, or software, or a combination of logic circuits, firmware, and software, within the control logic of a molecular scanner.

Figure 1:
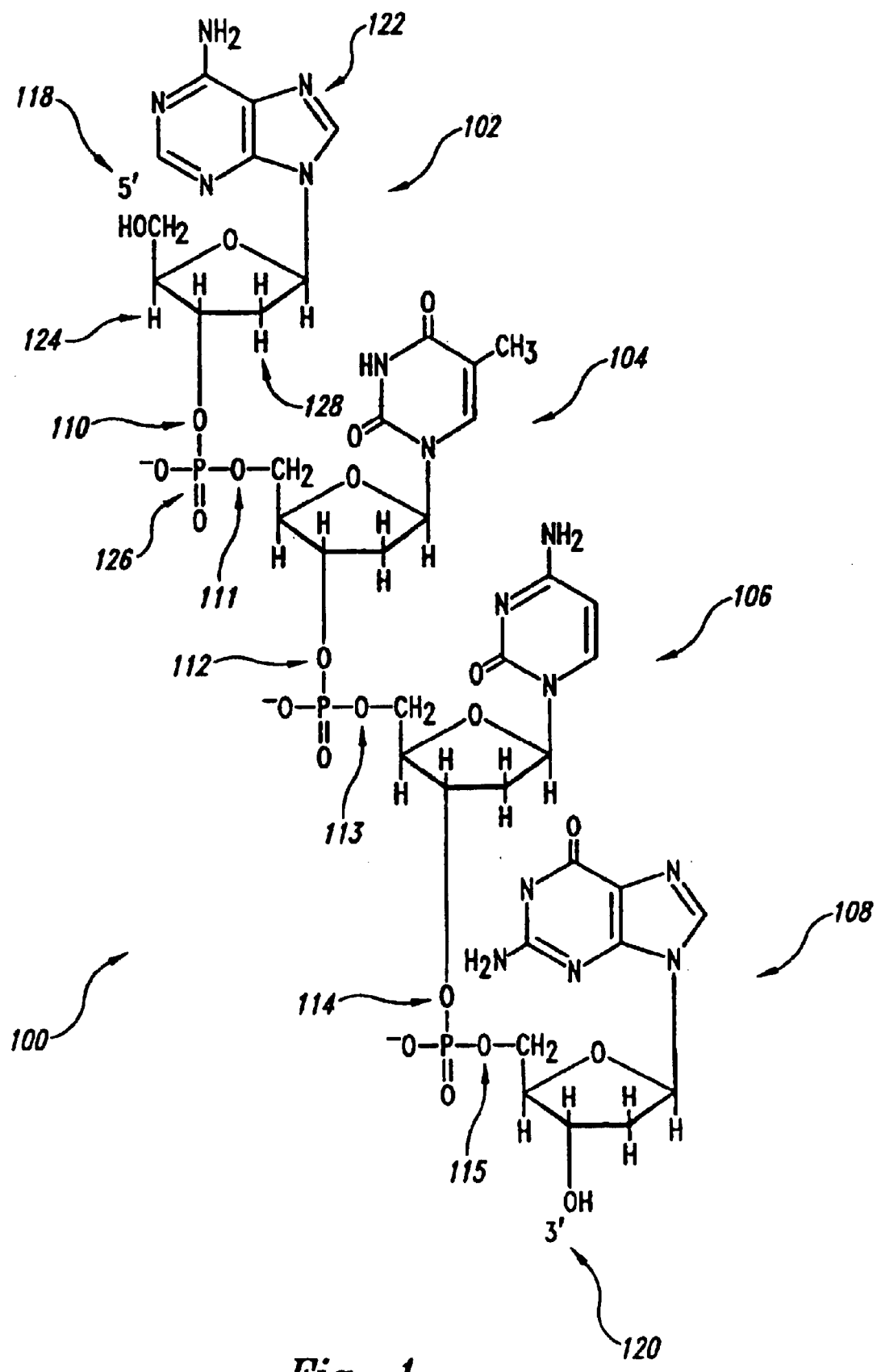
FIG. 1 illustrates a short DNA polymer 100, called an oligomer, composed of the following subunits: (1) deoxyadenosine 102; (2) deoxy-thymidine 104; (3) deoxycytosine 106; and (4) deoxy-guanosine 108.
Figure 2A:
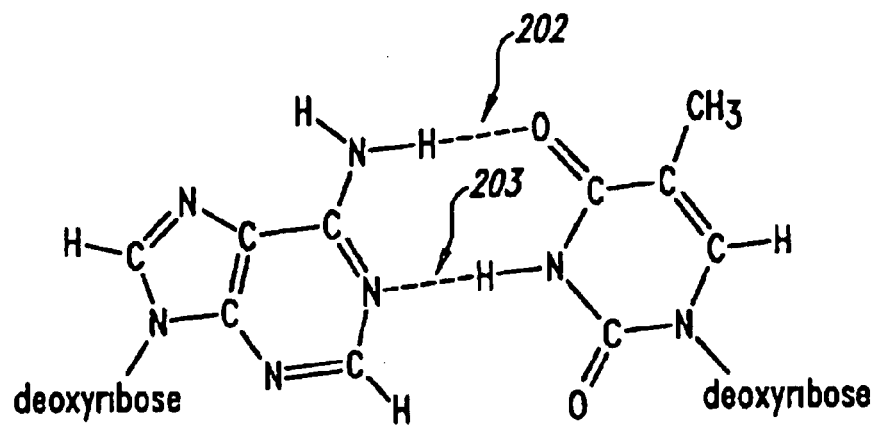
FIGS. 2A–B illustrate the hydrogen bonding between the purine and pyrimidine bases of two anti-parallel DNA strands.
Figure 2B:
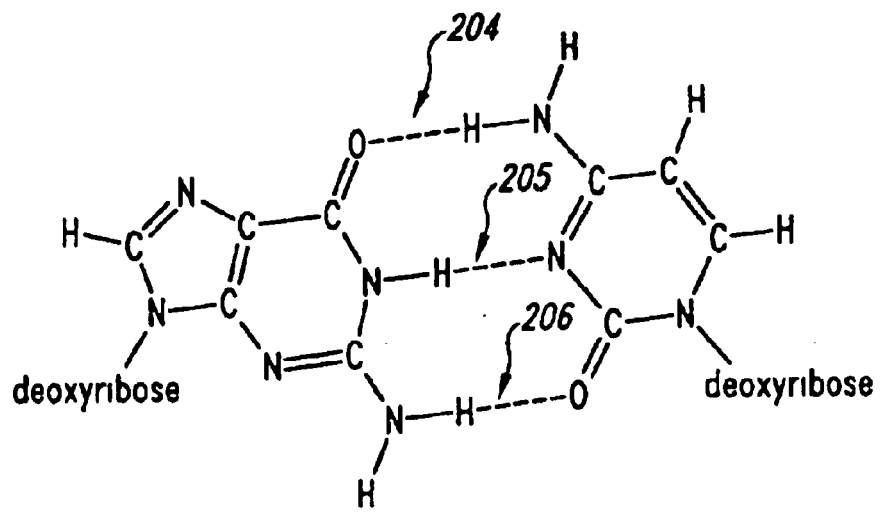
Figure 3:
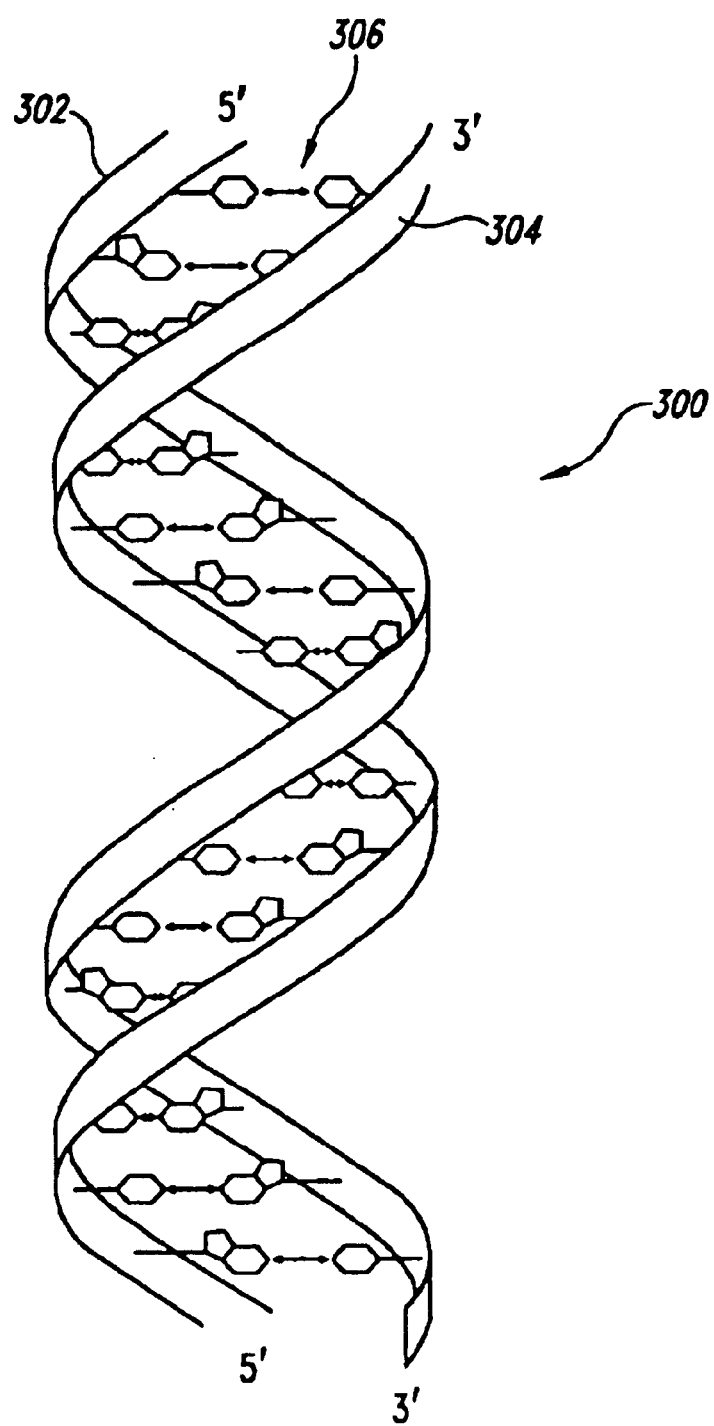
FIG. 3 illustrates a short section of a DNA double helix 300 comprising a first strand 302 and a second, anti-parallel strand 304.
Figure 4:
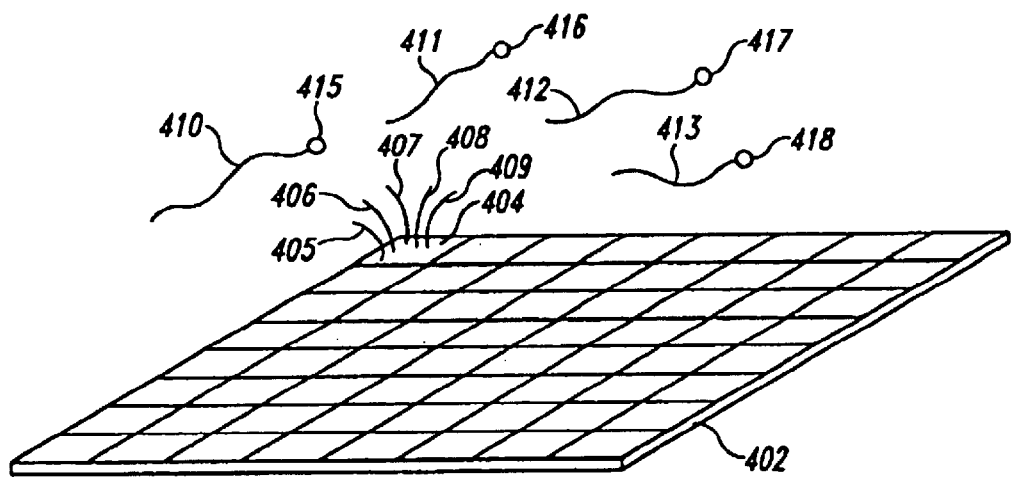
FIGS. 4–7 illustrate the principle of the array-based hybridization assay.
Figure 5:
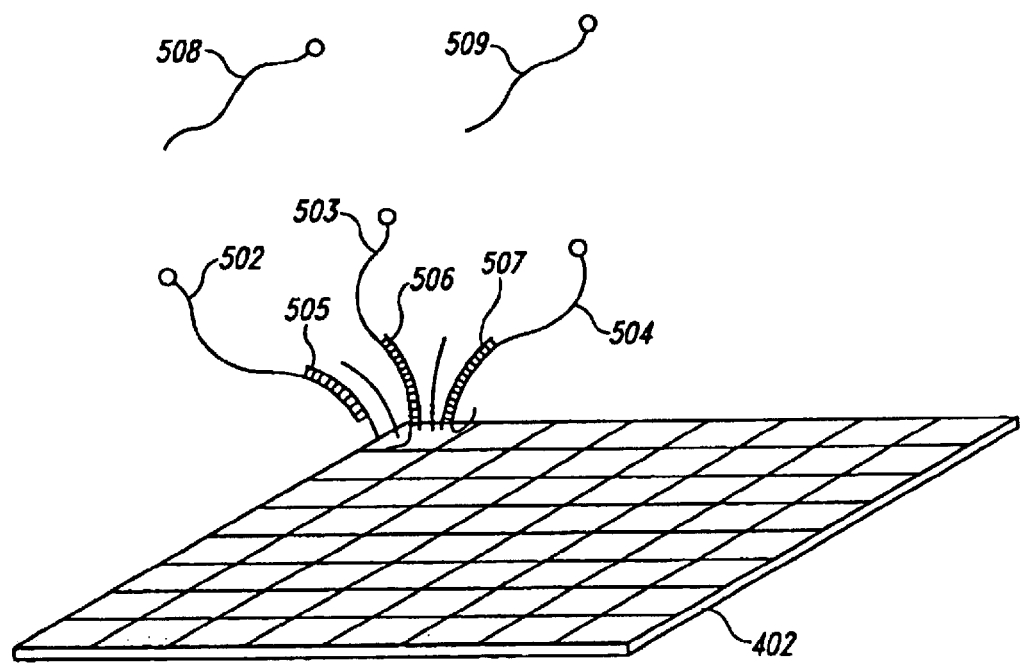
Figure 6:
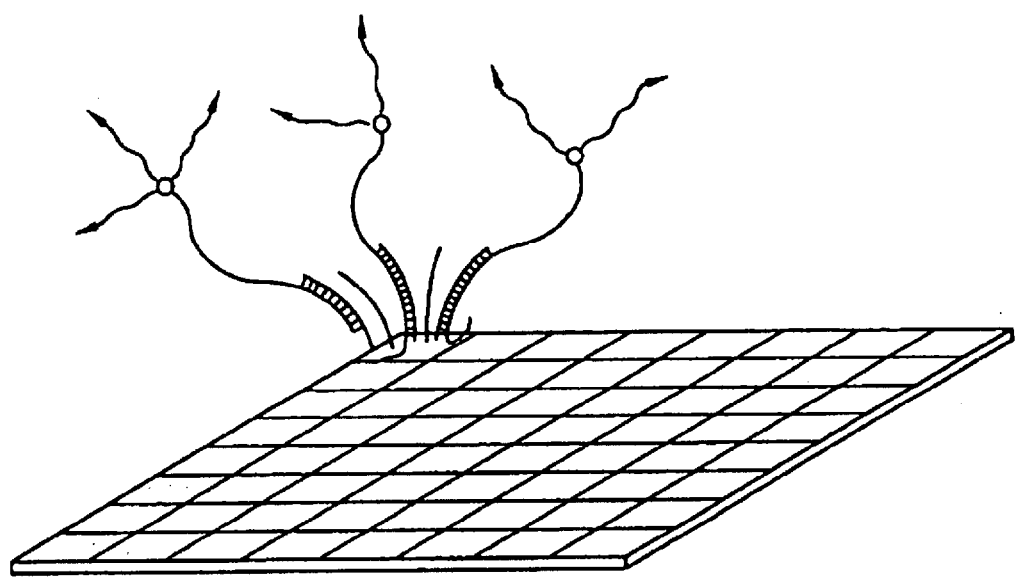
Figure 7:
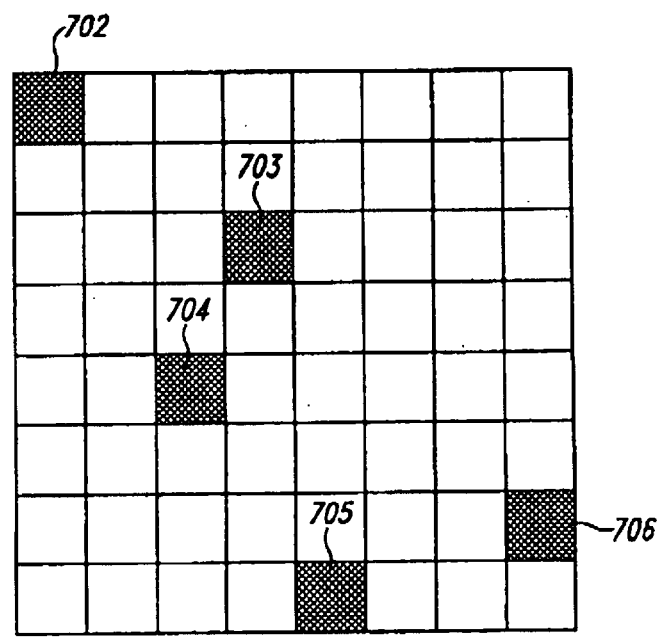
Figure 8:
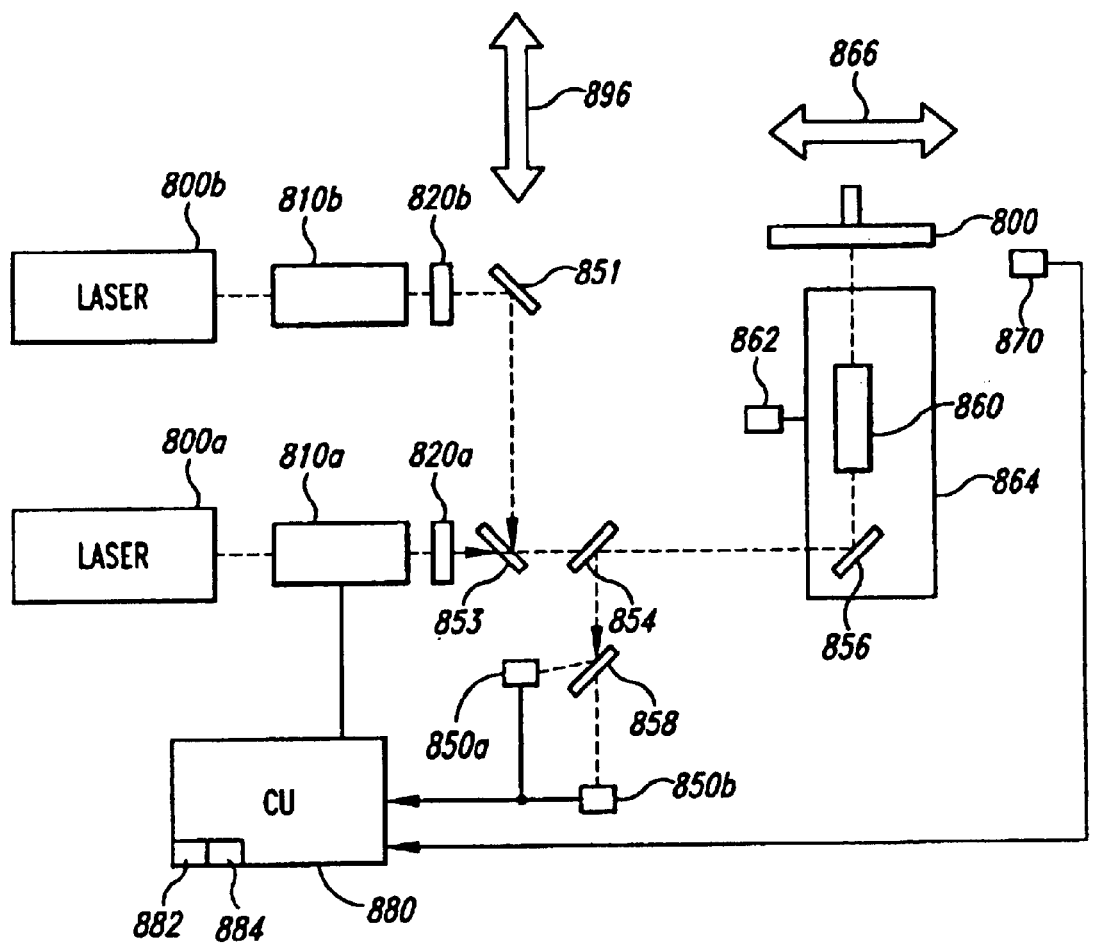
FIG. 8 is a block diagram of major optical and electronic components of a molecular array scanner.
Figure 9:
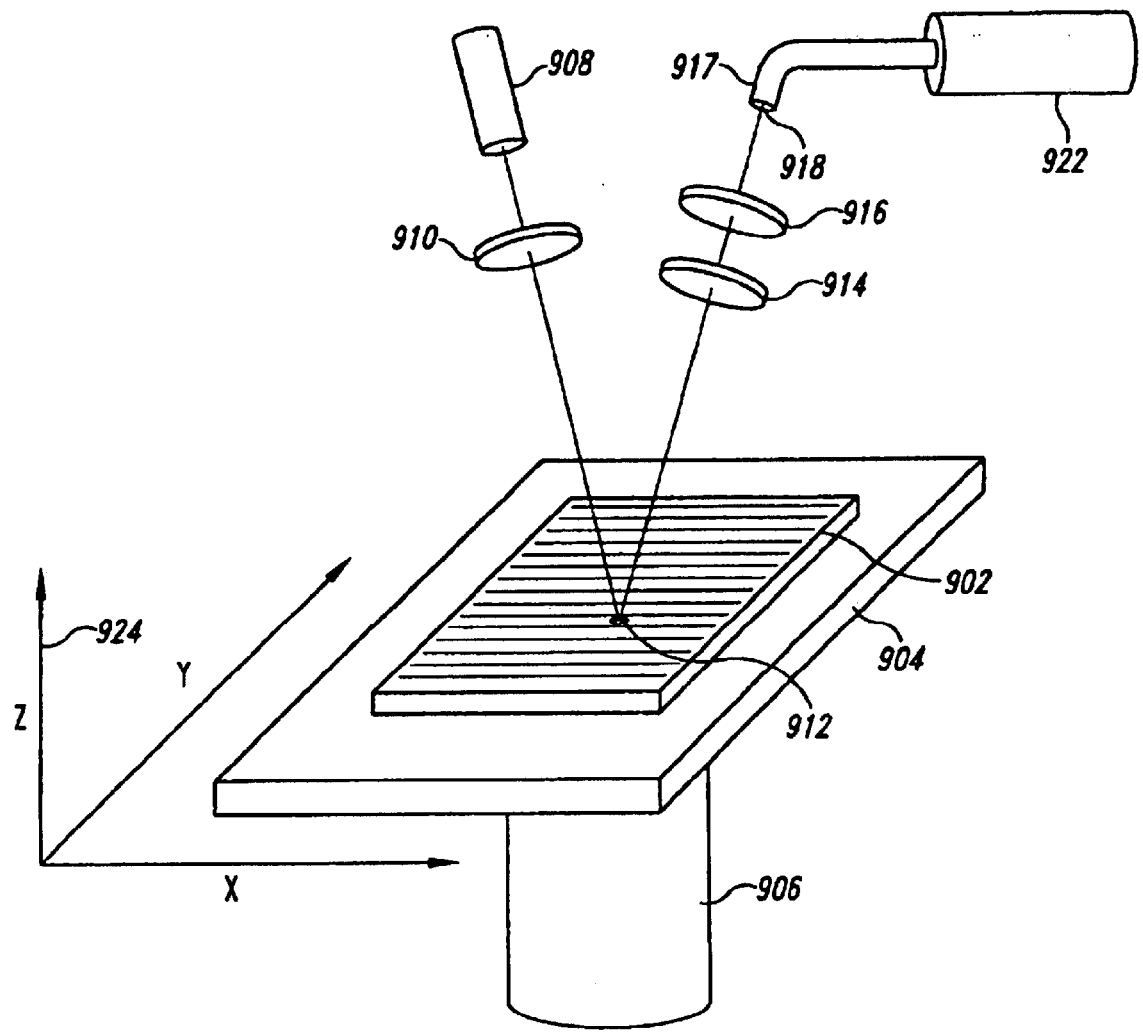
FIG. 9 abstractly illustrates the scanner components related to the automated focus-distance-determination method that represents one embodiment of the present invention.

FIG. 9 abstractly illustrates the scanner components related to the automated focus-distance determination method that represents one embodiment of the present invention. A molecular array 902 is mounted to the stage 904 of a molecular array scanner. The stage 904 can be translated vertically and horizontally in a plane coincident with the plane of the surface of the stage by X and Y translation mechanisms not shown in FIG. 9. In addition, the distance of the stage 904 from the optical fiber or other light-gathering medium can be controlled by a distance-control mechanism that moves the stage and stage support 906 in a direction perpendicular to the plane of the scanner.

Light from a laser 908, focused and filtered via various optic components 910, illuminates a small region of the array 912 from which light of a generally longer wavelength is emitted by fluorescent or chemiluminescent compounds incorporated into target molecules. The emitted light is filtered and focused by various optical components 914 and 916 into a roughly disk-shaped spot 918 that impinges on the surface of an optical fiber 920 or another light-collection medium that inputs emitted light from the surface of the molecular array into a photodetector 922.

An orthogonal x, y, z coordinate system 924 is shown near the left, lower corner of the molecular array-scanner stage 904 to indicate the directions in which the stage can be moved relative to the surface of the optical fiber 920 on which emitted light is focused. The exact functional relationship between variations in the distance from the emitted-light source to the surface of the optical fiber 920, closely related to the distance of the stage from the optical fiber 920, referred to as the z-position position of the stage, depends on the geometry of the laser, molecular array, and optical fiber geometries. However, the focus-distance is a continuous function of z-position. If the plane of the surface of the molecular array 902 is not parallel to the plane of the surface of the stage 904, then horizontal translations in the x, y plane of the stage may also affect the distance between light-emitting probe molecules on the surface of the molecular array and the optical fiber 920. The dynamic autofocus feedback-control mechanism within this scanner can dynamically adjust the z-position of the stage as the stage is translated in the x, y plane in order to correct for the small focus-distance variation during a scan due to molecular-array-surface irregularities and positioning and orientation problems that cause the plane of the surface of the molecular array to be inclined with respect to the plane of the surface of the stage. Thus, when an optimal focus-distance is determined, a molecular array can be scanned at this focus distance by the autofocus mechanisms within the scanner. Because the focus distance is a continuous function of the z-coordinate of the spatial location of the illuminated spot 912 of the molecular-array surface, which is, in turn, a continuous function of the z-position of the stage, the following discussion is related to optimizing the z-position of the stage 904. It should be noted that the following discussion and Figures could also be cast in terms of z-coordinate of the laser-illuminated region of a molecular array, or the distance of either the stage or the laser-illuminated region of a molecular array from the emitted-light-collection medium.

Figure 10:
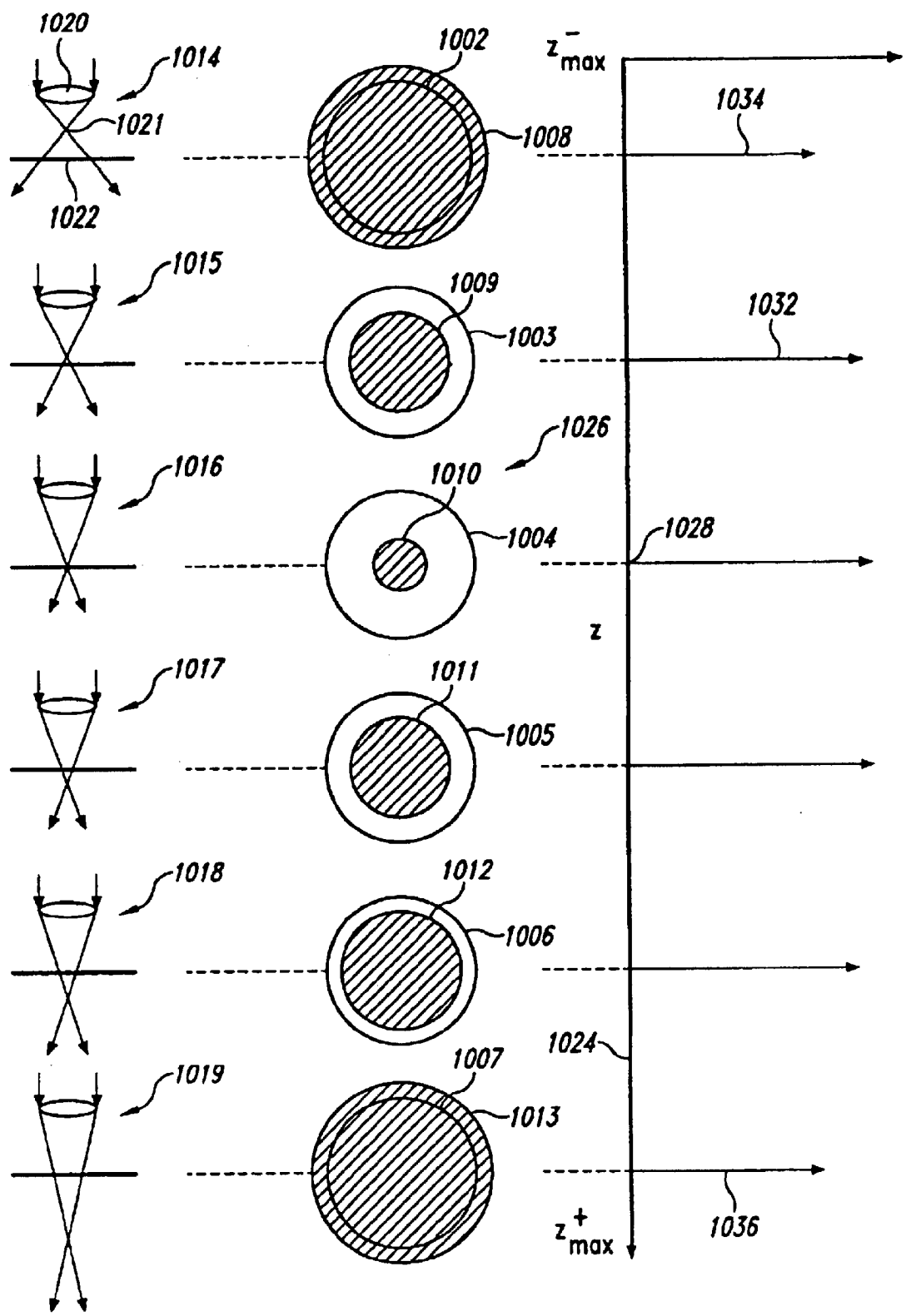
FIG. 10 illustrates the effect of small changes in the z-position of an illuminated spot on the surface of a molecular array with respect to the image of the emitted light from the illuminated spot of the surface of the molecular array focused on the surface of an optical fiber.

FIG. 10 illustrates the effect of small changes in the z-position of the stage, or z-coordinate of an illuminated spot on the surface of a molecular array, with respect to the position of the image of the emitted light from the illuminated spot of the surface of the molecular array focused onto the surface of an optical fiber. This is one example of how the measured intensity of the emitted light can vary with changes in the focal distance. Another example is the loss of emission-intensity due to the lack of correct focus of the illuminated spot on the surface of the molecular array.

In FIG. 10, the circular cross section of the surface of an optical fiber (920 in FIG. 9) is represented by circles 1002–1007. The image of an illuminated spot on the surface of the molecular array is shown in FIG. 10 by various differently sized, cross-hatch-filled circles 1008–1013. In FIG. 10, representations 1014–1019 of the focusing of the emitted light onto the plane of the circular cross section of the surface of the optical fiber are shown at the left. In each representation, a lens-like optic, e.g. lens-like optic 1020, focuses light to a point, e.g. point 1021, above, on, or below the plane, e.g. plane 1022, of the surface of the optical fiber. As the illuminated spot on the surface of the molecular array is moved in the z direction, the image of the illuminated spot focused onto the surface of the optical fiber, first defocused as illuminated spot 1008, focuses and decreases in diameter relative to the diameter of the cross section of the optical fiber. Illuminated spot 1010 represents a focused spot, corresponding to the optics representation 1016. As the illuminated spot on the surface of the molecular array is moved further in the z direction, the illuminated spot gradually defocuses and grows in diameter relative to the diameter of the cross section of the optical fiber. At either extreme of the z-position range, as indicated by optics representations 1014 and 1019, the image of the illuminated spot is sufficiently defocused that the image of the illuminated spot is larger than the cross section of the optical fiber, and emission photons representing a portion of the emitted-light are lost, resulting in a decrease in the intensity of the resulting measured signal. In FIG. 10, the z-positions that result in the corresponding respective sizes of the image of the illuminated spot and the cross section of the optical fiber plotted along a coordinate axis 1024 corresponding to the z-position of the stage of the molecular scanner. The z-positions range from a lowest value, $Z_{max}^-$, to a highest z value, $Z_{max}^+$. In FIG. 10, for example, the z-position of the stage resulting in a centered, focused image of the illuminated spot on the surface of the optical fiber 1026 is shown with z coordinate 1028. In FIG. 10, a vertical coordinate axis 1030 is shown orthogonal to the z-position coordinate axis 1024. This orthogonal coordinate axis corresponds to the intensity of the emitted light detected by a photodetector (922 in FIG. 9) of the molecular array scanner. In FIG. 10, the horizontal lines, such as horizontal line 1032, plotted along the vertical z-position axis represent the signal intensities measured for a particular region of the surface of the molecular array corresponding to the z-positions of the stage of the molecular array. Again, as the image of the illuminated region of the molecular array defocuses past the edges of the fiber, not all of the emitted light is captured by the fiber and, as a result, the intensities 1034–1036 of the signal level decreases proportionally to the fraction of light that is missing the fiber.

Figure 11:
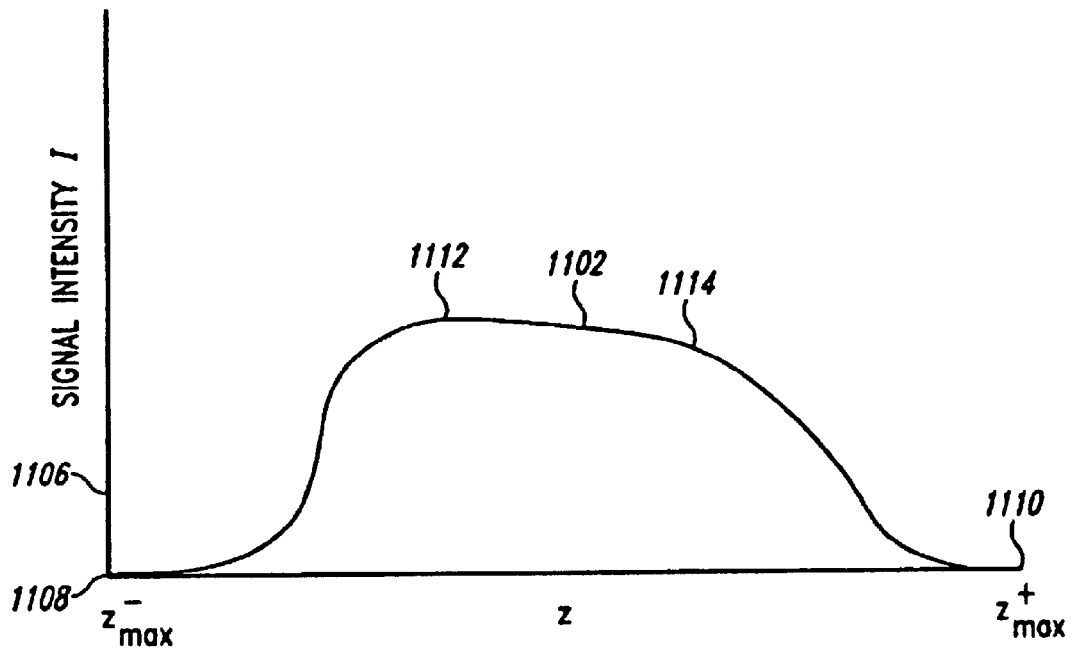
FIG. 11 shows a representation of the function of the signal intensity I measured by the photodetector of a molecular array scanner as a function of the z-position of an illuminated region of the molecular array that generates the signal.

The graph of signal intensity to z-position, as shown in FIG. 10, can be rotated 90 degrees and plotted as a continuous, rather than a discrete, function. FIG. 11 shows a representation of the function of the signal intensity I measured by the photodetector of a molecular array scanner as a function of the z-position of an illuminated region of the molecular array that generates the signal. The function illustrated in FIG. 11 1102 is exaggerated in order to clearly illustrate the general features of a typical signal-intensity-to-z-position ("I/z") relationship for one class of molecular array scanners. As in FIG. 10, the functional relationship is plotted from a $Z_{max}^-$ position to a $Z_{max}^+$ position along the z-position axis 1104, with the height of the curve representing the measured signal intensity with respect to the signal-intensity axis 1106. Proceeding rightward from the $Z_{max}^-$ position 1108 towards to the $Z_{max}^-$ position 1110, the signal intensity sharply rises to a signal intensity peak 1112 and then falls gradually to the edge 1114 of a steeply descending curve that falls back to nearly 0 intensity at $Z_{max}^{30}$. In one class of molecular array scanners, the I/z function appears as a mesa, with the top of the mesa (section of the curve between 1112 and 1114 in FIG. 11) slanted slightly downward.

Figure 12:
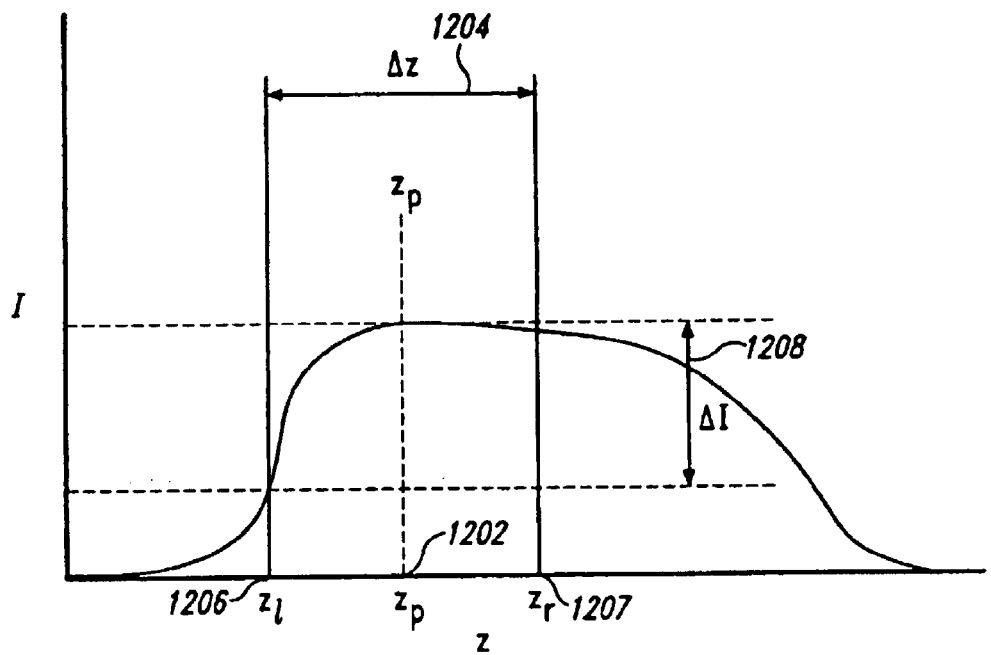
FIG. 12 illustrates the variation in signal intensity I with z-position z in the vicinity of the peak of the $I_z$ curve.

The autofocus mechanism within a molecular array scanner, as with all electromechanical devices, is not infinitely precise. Instead, the autofocus mechanism is capable of maintaining the distance of the illuminated portion of a molecular array surface within a small range of distances by controlling the z-position of the stage. Thus, despite the autofocus mechanism, the z-position, functionally related to the focus distance, varies slightly over the course of a molecular array scan. FIG. 12 illustrates the variation in signal intensity I with z-position z in the vicinity of the peak of the I curve. In FIG. 12, the z coordinate for the peak, $z_p$, is plotted on the z axis 1202. The total variation in z-position during a scan is shown by the interval $\Delta z$ 1204 plotted from $z_l$ to $z_r$ on the z axis 1206–1207. The signal intensity varies over the interval $\Delta z$ 1204 by a corresponding signal intensity interval $\Delta I$. Note that, for the typical I/z functional relationship illustrated in FIG. 12, the signal intensity varies over the entire $\Delta I$ interval 1208 within the portion of the $\Delta z$ interval to the left of the peak position $Z_p$, while varying only relatively slightly in the portion of the $\Delta z$ interval to the right of the peak position $Z_p$. Thus, because of the asymmetry of the I/z curve with respect to the peak position $Z_p$, small fluctuations in the focus distance corresponding to $Z_p$ may result in relatively large variation in signal intensity.

Figure 13:
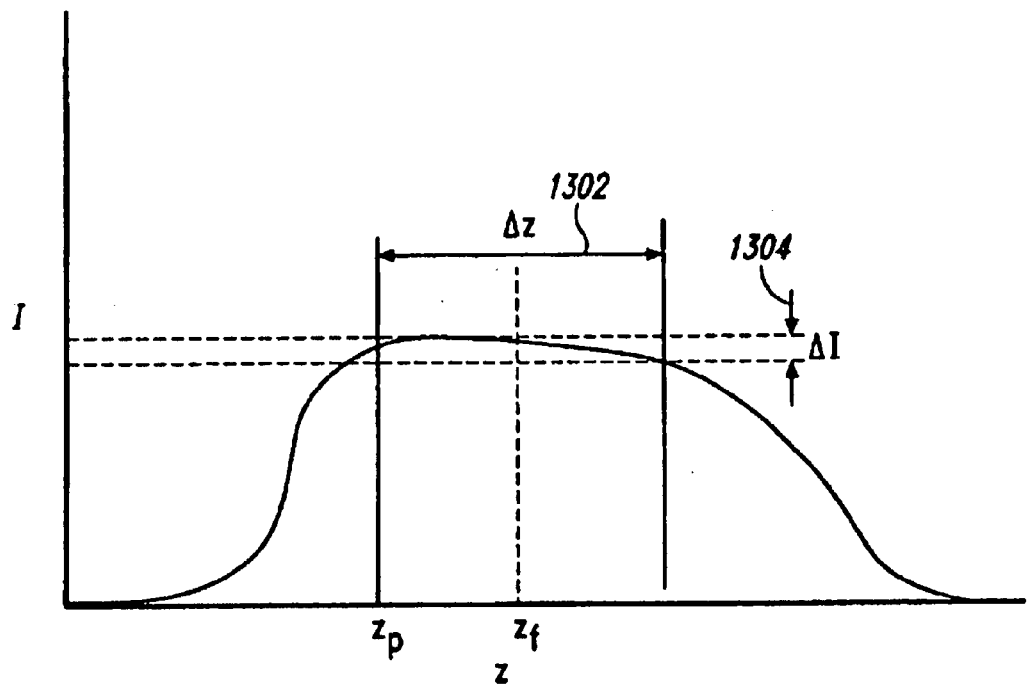
FIG. 13 illustrates selection of an optimal focus distance $Z_p$.

It is desirable to select a focus distance that provides a relatively slight variation in signal intensity corresponding to slight variations in focus distance during scanning of a molecular array. It is the goal of an autofocus mechanism to help maintain a constant system sensitivity for a constant quantity of flurophore over the entire surface of a molecular array. FIG. 13 illustrates selection of an optimal focus distance $Z_f$. As shown in FIG. 13, if the optimal focus distance $Z_f$ is chosen roughly centered in the interval representing the top of the mesa of the I/z curve, producing a $\Delta z$ interval 1302 within the top of the mesa, then the variation in signal intensity $\Delta I$ 1304 over the interval $\Delta z$ is relatively small compared with the $\Delta I$ interval (1208 in FIG. 12) resulting from selection of the focus distance at the peak of the I/z curve $Z_p$.

Figure 14:
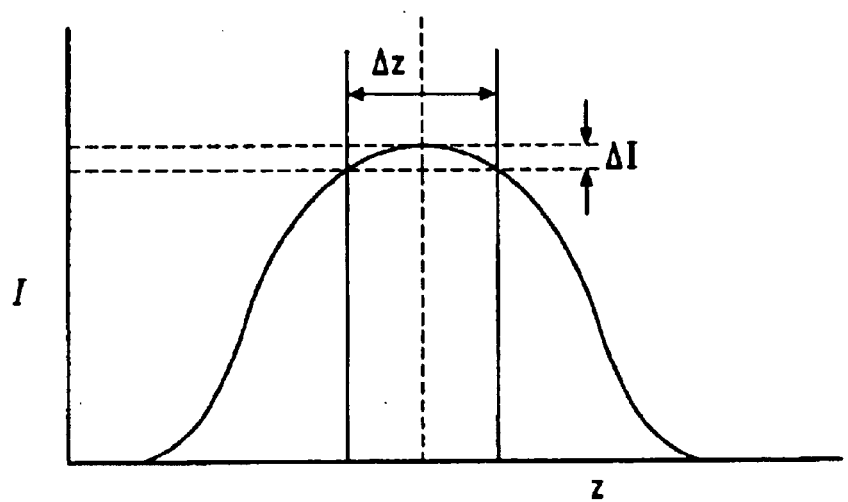
FIG. 14 illustrates the signal intensity variation over a z-position variation centered about the peak of the I/z curve.

If, by contrast, the scanner geometry and photo-detection apparatus produces a symmetrical, Gaussian-like I/z functional curve, selection of a focus distance corresponding to the z-position of the curve peak $Z_p$ may result in the smallest possible signal intensity variation. FIG. 14 illustrates the signal intensity variation over a z-position variation centered about the peak of the I/z curve.

Thus, either a focus distance corresponding to a z-position at a positive offset from the peak z-position may be selected, for I/z curves having slanted mesa forms, or a focus distance corresponding to the peak z-position may be optimal for symmetrical, Gaussian-like I/z functional relationships. In either case, the optimal focus distance is a focus distance that gives a relatively large signal intensity that varies relatively slightly with variation in the focus distance.

The method for optimal focus distance selection that represents one embodiment of the present invention relies on a single-pass, automated scan of a reference molecular array. The reference molecular array is prepared by precisely coating the surface of a molecular array substrate with a polymethylmethacrylate polymer ("PMMA") containing a fluorescent or chemiluminescent dye. The PMMA polymer can be spun onto the surface of a slide and, if necessary, planarized, using PMMA-substrate-preparation techniques commonly employed in the manufacture of semiconductors. PMMA-based reference arrays are far more uniform than previously employed cyanine-dye reference arrays. The U.S. patent application Ser. No. 10/008598 entitled "Devices For Calibrating Optical Scanners And Methods Of Using The Same" by Holcomb et al. (filed Dec. 4, 2001) details the PMMA-based reference arrays, and is herein incorporated by reference.

Figure 15:
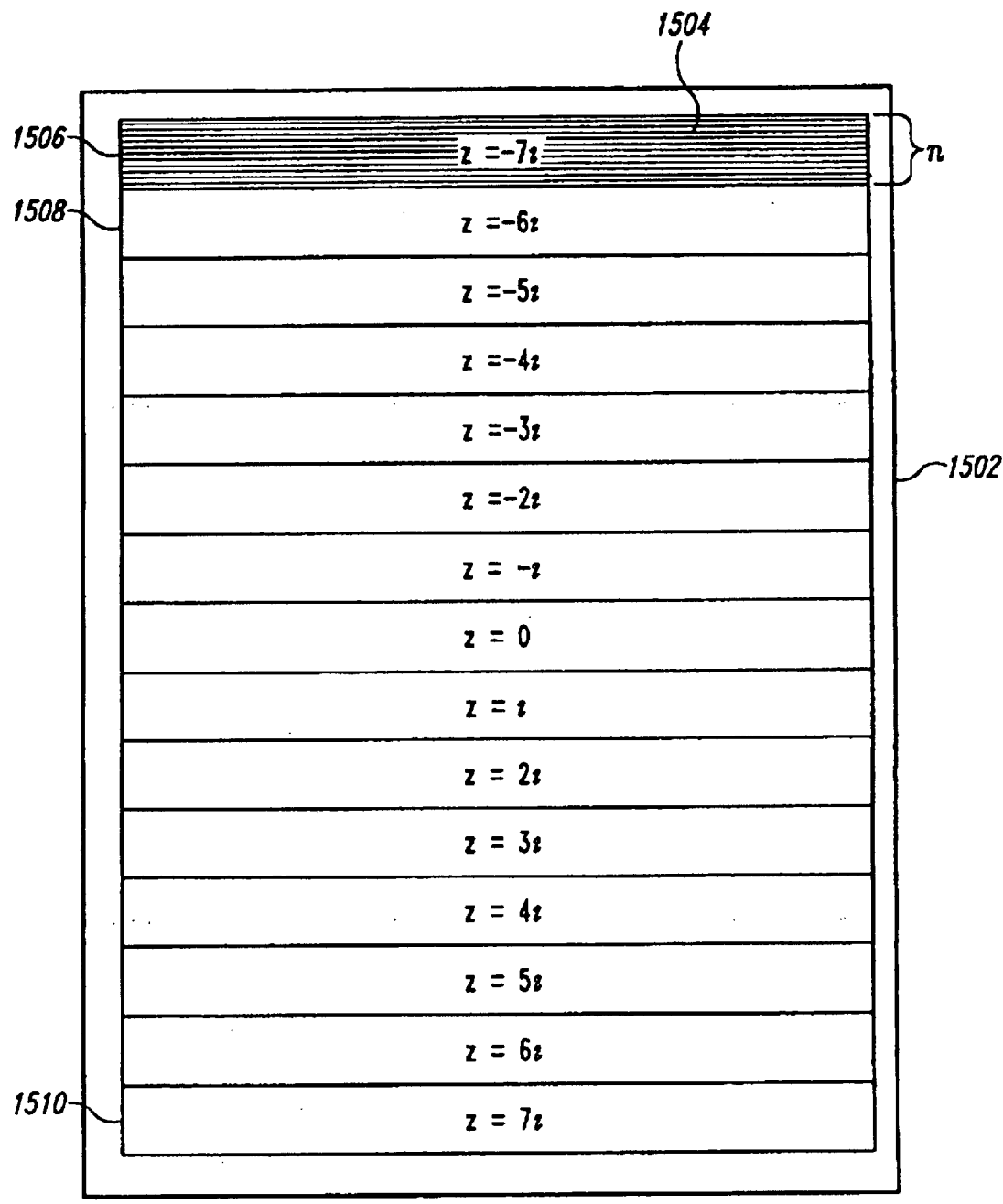
FIG. 15 illustrates the scan pattern employed in a preferred embodiment of the present invention.

FIG. 15 illustrates the scan pattern employed in a preferred embodiment of the present invention. In FIG. 15, a molecular array 1502 is abstractly represented with horizontal rows, such as row 1504. The scan pattern involves scanning a fixed number of contiguous rows n at each z-position over a range of z-positions $Z_{max}^-$ to $Z_{max}^+$. The z-position is incremented by an increment i over this range of z-positions. For example, as shown in FIG. 15, a contiguous block of n rows is first scanned at z-position z=−7i, a second block of n contiguous rows is scanned at z-position z=−6I 1508, and so on, up through scanning of the continuous block of n rows 1510 at z-position z=7i. The number of rows scanned at each z-position n, the z-position increment i, and the range $Z_{max}^-$ to $Z_{max}^+$ may all be specified in a configuration file for the automated focus-distance determination. Note that there are many alternative possible focus-distance-determination scan patterns. In one embodiment of the present invention, z positions ranging from $-20\mu$ (microns) to $+20\mu$ are scanned at $0.25\mu$ increments, with ten rows scanned for each z-position.

In the following discussion, the described embodiment relates to a two-channel molecular array scanner that measures emitted light in red and green regions of the visible spectrum. Thus, the following discussion refers to red and green channels and red and green signals. However, the present invention is equally applicable to single-channel molecular array scanners or to molecular array scanners that measure more than two types of signals, or measure signals from different parts of the electromagnetic radiation spectrum.

Figure 16:
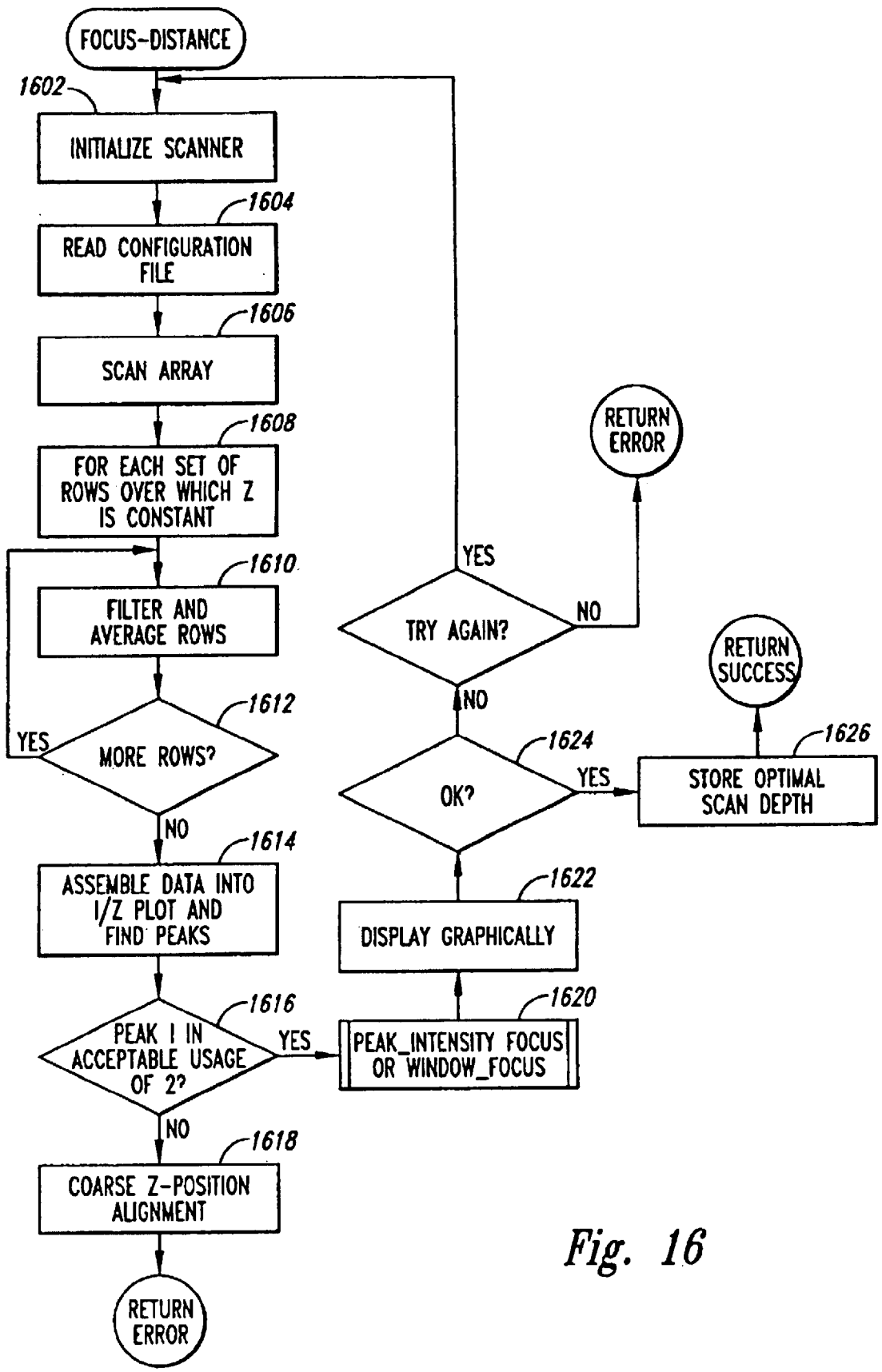
FIG. 16 is a flow-control diagram for the optimal focus-distance determination method "focus_distance" that represents one embodiment of the present invention.

FIG. 16 is a flow-control diagram for the optimal focus-distance determination method "focus_distance" that represents one embodiment of the present invention. In step 1602, the scanner is initialized. Initialization involves checking the scanner to make sure that the scanner is properly physically configured, setting the photodetector voltages to default voltages, initializing a stage motion controller(s), and loading the reference molecular array into the scanner and verifying, via a bar code imprinted on the surface of the molecular array, that the reference molecular array is the appropriate reference molecular array for the optimal focus-distance determination. In step 1604, the optimal focus-distance determination configuration file is input, specifying various parameters for the optimal focus-distance determination, including the parameters n, i, $Z_{max}^-$ and $Z_{max}^-$ parameters described with reference to FIG. 15, above. In step 1606, the reference array is scanned as specified by the configuration-file parameters input in step 1604. The reference-array scan results in a computer encoding of signal intensities measured for discrete regions covering the surface of the molecular array. In many molecular array scanners, these signal-intensity results are encoded as integer or floating-point values associated with pixels within the scanned image of the molecular array. In the for-loop comprising steps 1608, 1610, and 1612, focus_distance filters and averages the signal intensities for each block of n rows. The rows are filtered to remove saturated pixels, or, in other words, pixels with intensity values that exceed the linear range of the electronics (due, for example, to dust), and the signal intensities of the remaining pixels are averaged to produce an average intensity value corresponding to the z-position at which the rows were scanned. Note that, if the number of saturated pixels exceeds some specified threshold, the scan may be rejected, and an indication displayed by the molecular array scanner to a user indicating that the molecular array scanner needs to be reconfigured in order to produce signal intensities within appropriate ranges.

Next, in step 1614, the average intensity values for each z-position are assembled into a computer-encoded format corresponding to the I/z graphs shown in FIGS. 11–13 and 14, above. Note that each type of signal, such as the red and green signals described above, in the background section, are measured to produce separate I/z functional relationship for each type of signal, or channel. The computer-encoded data representing the I/z functional relationship for each channel can then be scanned with respect to z-position to determine the I and z coordinates of the peak of the I/z curve. In step 1616, focus_distance determines whether the z-positions of the I/z peaks for all channels fall within an acceptable range of z-position values. If not, then focus_distance displays an error message in step 1618 indicating the need for resetting the coarse adjustment of the z-component of the autofocus mechanism, or another resetting or reconfiguration of the molecular array scanner, and then returns an error. If all the peaks fall within an acceptable z-position range, then a focus routine is called in step 1620. The focus routine called depends on the geometry and configuration of the molecular array scanner. For molecular array scanners that produce mesa-shaped I/z functional curves, the routine "window_focus" is called. Alternatively, if the molecular array scanner produces symmetrical, Gaussian-like curves, as shown in FIG. 14, then the focus routine "peak_intensity_focus" is called. Molecular scanners that produce other types of I/z curves may need other, specific focus routines. The focus function called in step 1620 produces an optimal z-position corresponding to an optimal focus distance, $Z_f$, that can be used by the molecular array scanner for one or more data-acquisition scans.

Next, in step 1622, focus_distance graphically displays the results of the optimal focus-distance determination to a user. If the user wishes they can review the displayed information and can input acceptance or rejection of the optimal focus-distance determination. If the method is found to be robust enough for any particular configuration of scanner, this step can be skipped and the process be fully automated. If the optimal focus-distance determination is accepted, as determined in step 1624, then the optimal focus distance is stored into non-volatile memory within the array scanner in step 1626, and focus_distance returns success. The optimal focus distance may be stored in flash memory, for example, or in other non-volatile memory storage, such as a mass storage device. If the optimal focus distance is rejected, as determined in step 1624, then the user is prompted for input as to whether to retry the optimal focus-distance determination. If the user elects not to retry the optimal focus-distance determination then focus_distance returns an error. Otherwise, control flows back to the initial step, step 1602.

Figure 21:
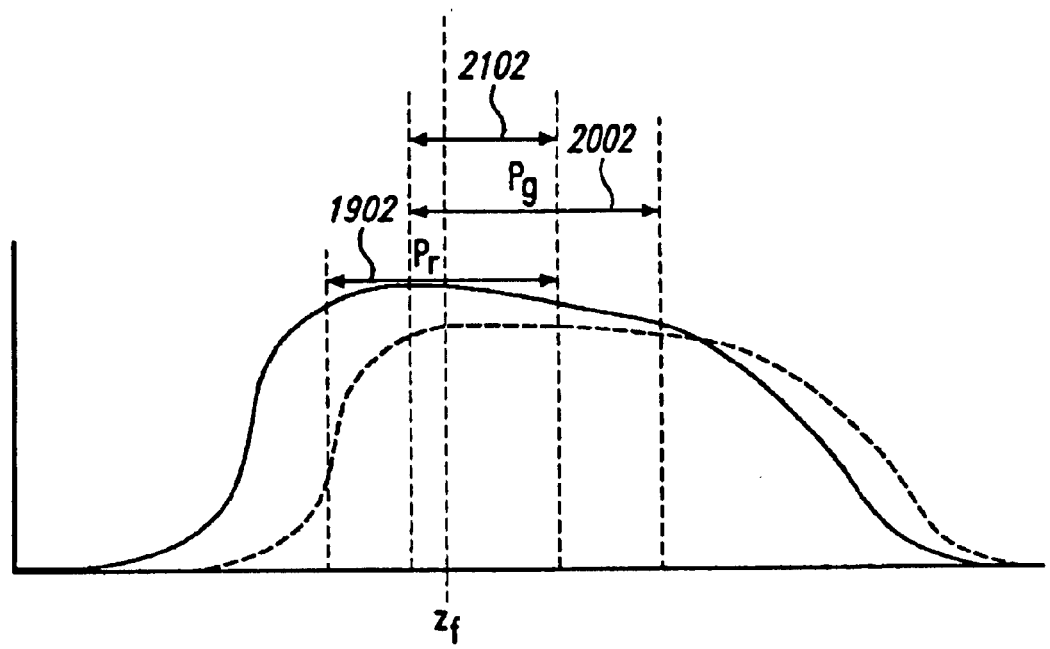
Figure 22:
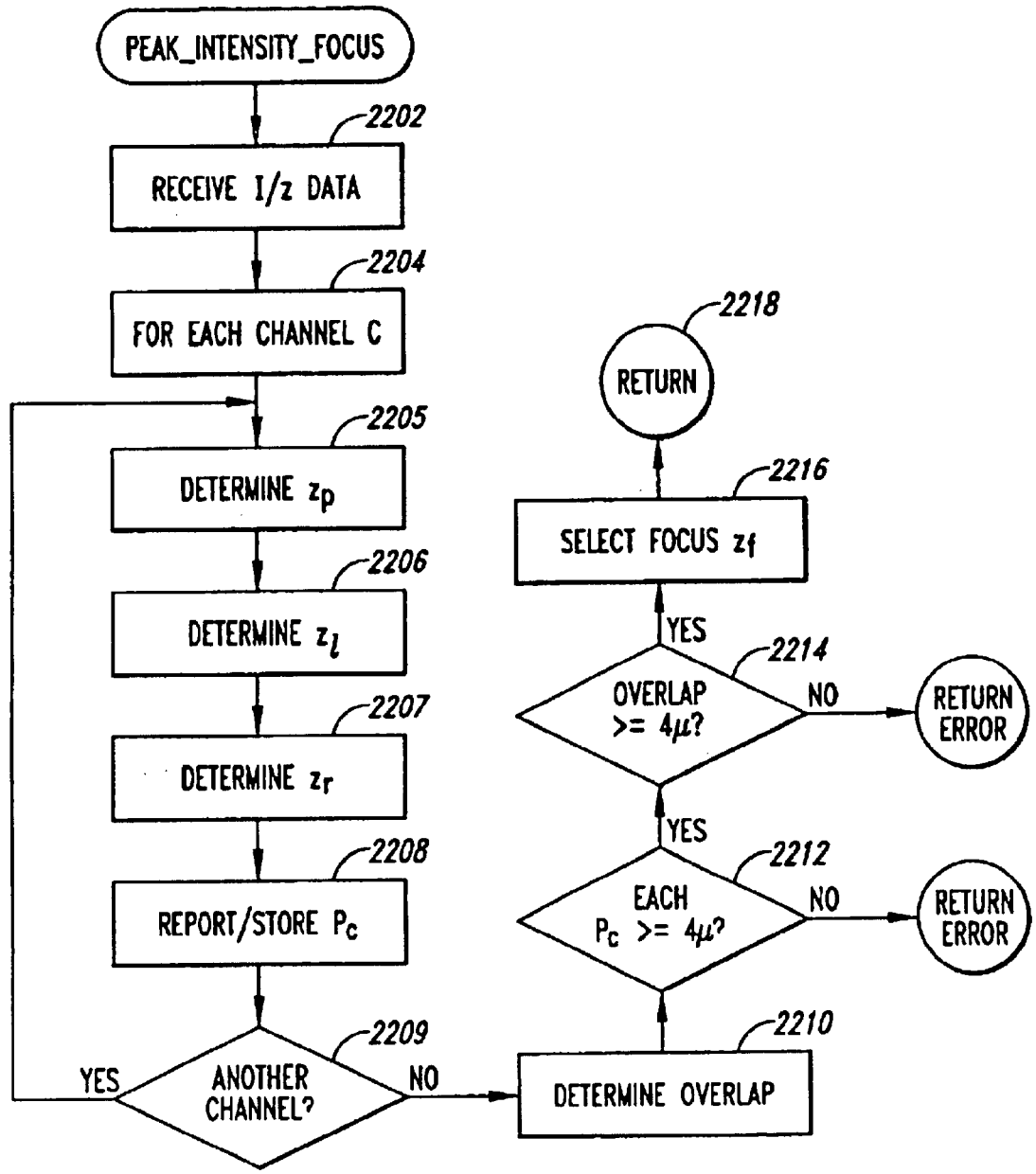
FIG. 22 is a flow-control diagram for the routine "peak_intensity_focus."

For molecular scanners that produce Gaussian-like, roughly symmetrical I/z curves, as shown in FIG. 14, the focusing routine "peak_intensity_focus" is called from step 1620 of focus_distance, described with reference to FIG. 16. FIGS. 17–21 illustrate operation of the routine "peak_intensity_focus" with reference to I/z functional curves. FIG. 22 is a flow-control diagram for the routine "peak_intensity_focus." Note that the I/z curves shown in FIGS. 17–21 are mesa-shaped curves characteristic of one class of molecular array scanners. Although the routine "peak_intensity_focus" provides best results for symmetrical, Gaussian-like I/z curves, it can also be applied to the mesa-shaped curves shown in FIGS. 17–21.

Figure 17:
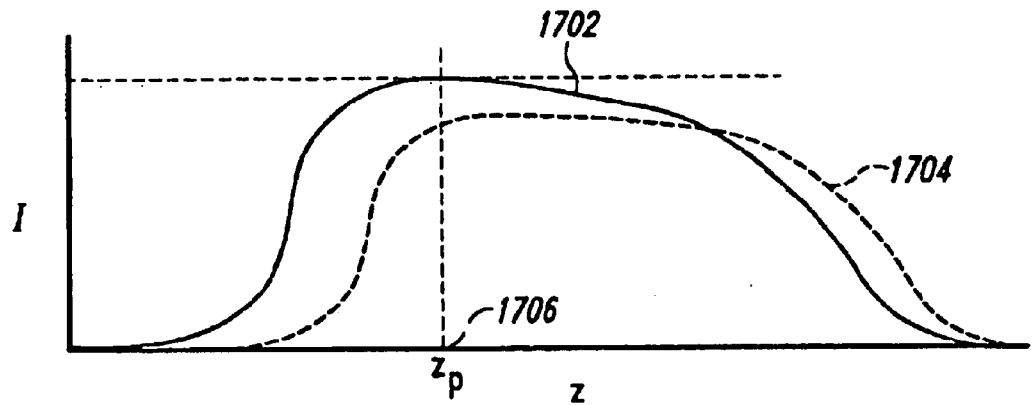
FIGS. 17–21 illustrate operation of the routine "peak_intensity_focus" with reference to I/z functional curves.
Figure 18:
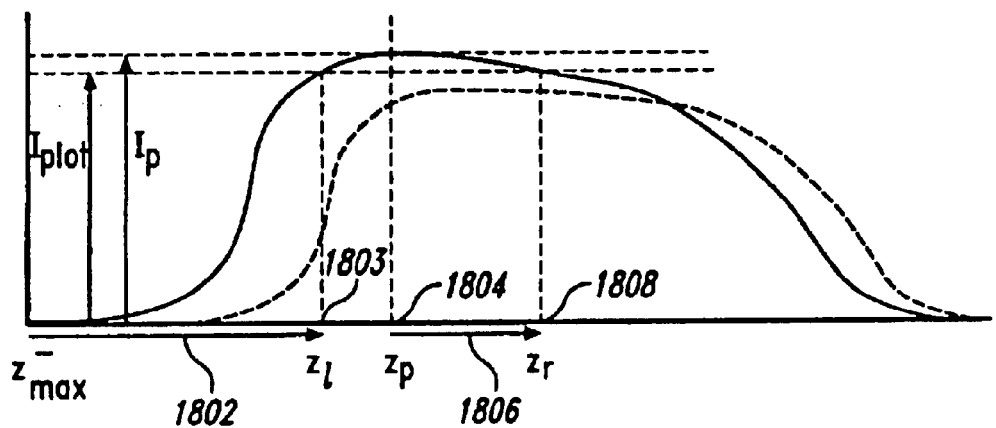
Figure 19:
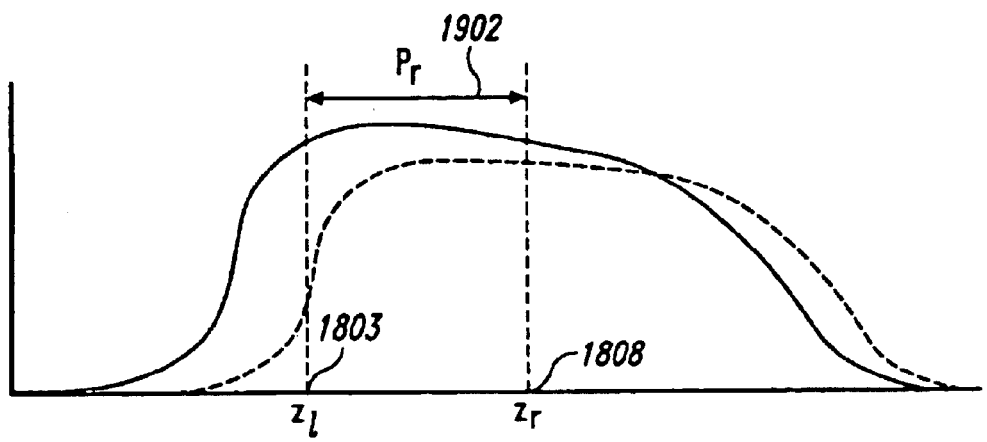
Figure 20:
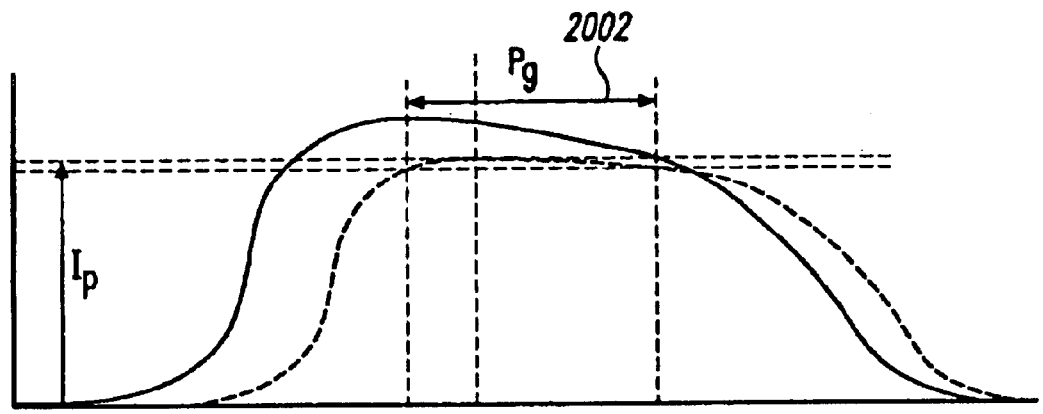

FIG. 17 is a graph of the I/z curve for the red channel 1702 and the I/z curve for the green channel 1704 of a two-channel molecular array scanner. The routine "peak_intensity_focus" first determines the z-position $Z_p$ 1706 of the peak in intensity for the red-channel I/z curve 1702, as shown in FIG. 17. Next, as shown in FIG. 18, peak_intensity_focus begins from the z-position $Z_{max}^-$ and proceeds rightward, as shown by arrow 1802, searching for a $Z_l$ z-position at which the corresponding signal intensity rises to a threshold percentage of the signal intensity corresponding to the $Z_p$ peak z-position. After finding the z-position $Z_l$, peak_intensity_focus starts at z-position $Z_p$ 1804 and proceeds rightward, as indicated by arrow 1806, evaluating the signal intensities of successive z-positions until peak_intensity_focus identifies a position $Z_r$ 1808 at which the corresponding signal intensity falls below the threshold value. As shown in FIG. 19, the z-positions $Z_l$ 1803 and $Z_r$ 1808 define endpoints of a red-channel plateau interval $P_r$ 1902 for the red-channel I/z curve. In similar fashion, peak_intensity_focus applies the plateau-finding technique to identify a green-channel plateau interval $P_g$ shown as interval 1202 in FIG. 20. Finally, as shown in FIG. 21, peak_intensity_focus determines whether the overlap 2102 between the red-channel plateau interval $P_r$ 1902 and green-channel plateau interval $P_g$ 2002 is greater than or equal to a threshold length, in microns, and determines whether or not each of plateau intervals $P_r$ and $P_g$ are also greater than or equal to a threshold width, in microns. In one embodiment, the threshold width for both the overlap 2102 and the plateau intervals 1902 and 2002 is four microns. If the overlap and plateau intervals do not meet the threshold requirements, then peak_intensity_focus returns an error value. Otherwise, in one embodiment, peak_intensity_focus returns a focus $Z_f$ corresponding to the z-position of the midpoint of the red-channel plateau interval 1902.

The routine "peak_intensity_focus" is alternatively described by the flow-control diagram of FIG. 22. In step 2202, peak_intensity_focus receives the I/z for each channel scanned by the molecular array scanner. In the for-loop comprising steps 2204–2209, peak_intensity_focus determines the plateau interval for each channel. In step 2205, peak_intensity_focus determines the z-position $Z_p$ corresponding to the peak intensity for the currently considered channel c. In steps 2206 and 2207, peak_intensity_focus determines the $Z_l$ and $Z_r$ z-positions for the plateau interval for the currently considered channel c, as described above with reference to FIGS. 18–19. Then, in step 2208, peak_intensity_focus reports and stores the plateau interval $P_c$ for the currently considered channel c. In step 2209, peak_intensity_focus determines whether or not the plateau for another channel needs to be computed and, if so, control flows back to step 2205. When all the plateau interval shave been computed, peak_intensity_focus, in step 2210, determines the overlap between the calculated and stored plateau intervals for all channels considered in the for-loop comprising steps 2204–2209. In step 2212, peak_intensity_focus determines whether or not each plateau interval is greater than or equal to a threshold value, in one embodiment, 4 microns. If not, then an error is returned. Otherwise, in step 2214, peak_intensity_focus determines whether or not the overlap, calculated in step 2210, is greater than or equal to a threshold value, in one embodiment, also 4 microns. If not, then an error is returned. Otherwise, a focus z-position $Z_f$ is selected in step 2216. In one embodiment, the midpoint of the red-channel plateau interval is selected as the focus $Z_f$. In other embodiments, a centroid z-position for the plateau intervals or for the overlap may be selected as the focus $Z_f$. In all embodiments, peak_intensity_focus returns the final selected focus $Z_f$ in step 2218.

Figure 30:
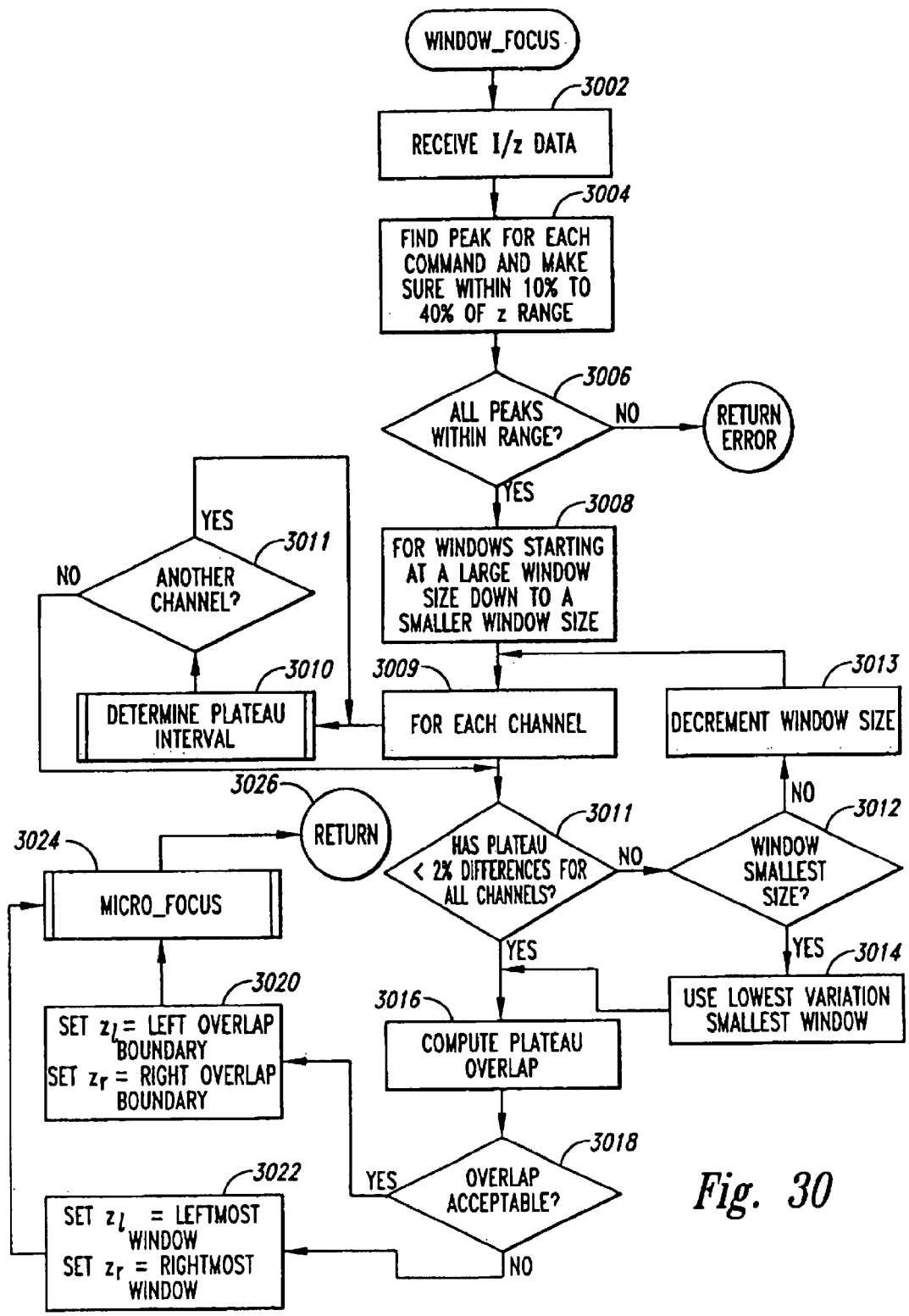
FIGS. 30–31 show flow-control diagrams that describe operation of window_focus.
Figure 31:
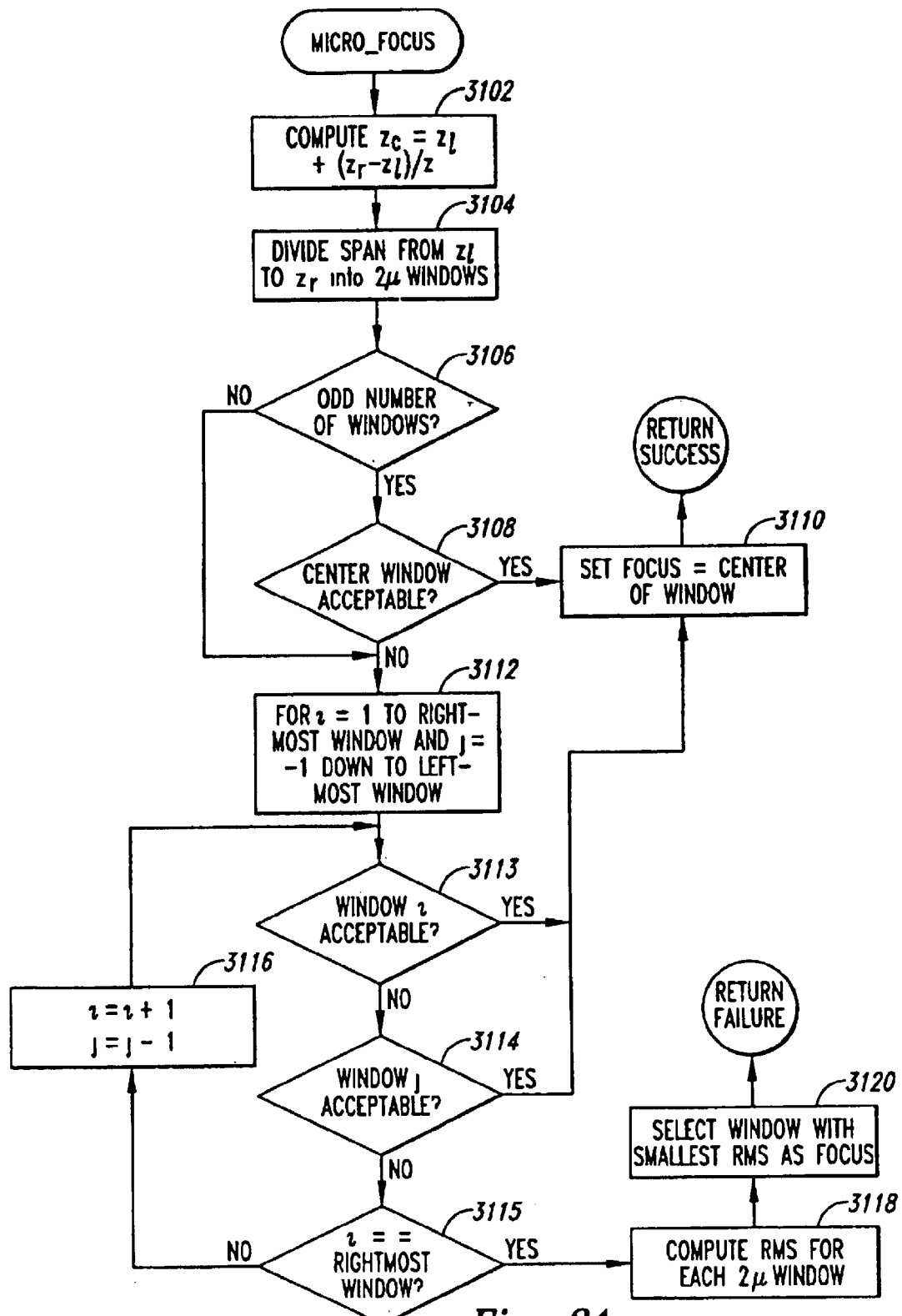

An alternate focus-finding routine is the focus-finding routine "window_focus," also called in step 1620 of the routine focus_distance illustrated in FIG. 16. The routine "window_focus" is more suitable for the mesa-shaped I/z curves characteristic of one class of molecular array scanners, for reasons described above with respect to FIGS. 12 and 13. FIGS. 23–29 illustrate operation of window_focus using graphical representations of I/z curves. FIGS. 30–31 show flow-control diagrams that describe operation of window_focus.

Figure 23:
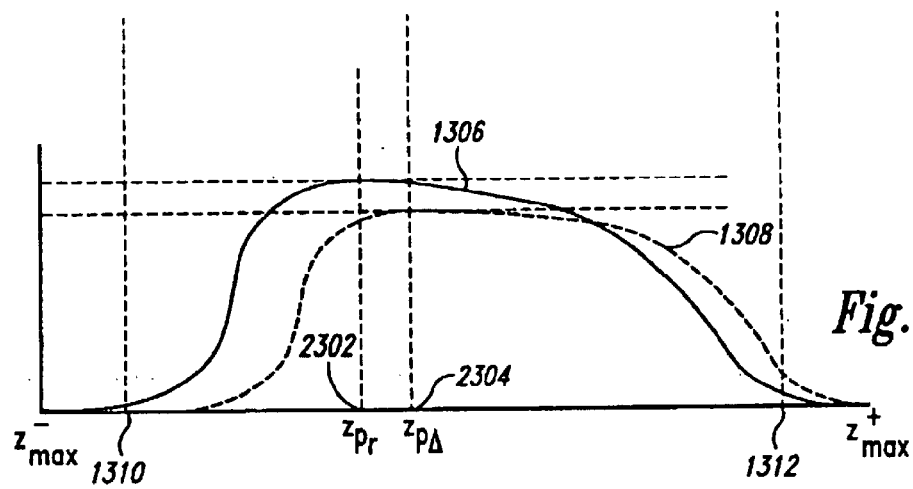
FIGS. 23–29 illustrate operation of window_focus using graphical representations of I/z curves.

In a first step, as shown in FIG. 23, window_focus computes the z-positions $Z_{P_r}$ and $Z_{P_g}$ 2302 and 2304 for the red-channel I/z curve 1306 and the green-channel I/z curve 1308, respectively. FIGS. 23–29 assume a two-channel molecular array scanner. Then, window_focus checks to make sure that these peak positions $Z_{P_r}$ and $Z_{P_g}$ fall within a range of z-position values 1310 and 1312 that represents 80 percent of the range $Z_{max}^+ - Z_{max}^-$. If the peak z-positions $Z_{P_r}$ and $Z_{P_g}$ fall outside this range, an error is returned.

Figure 24:
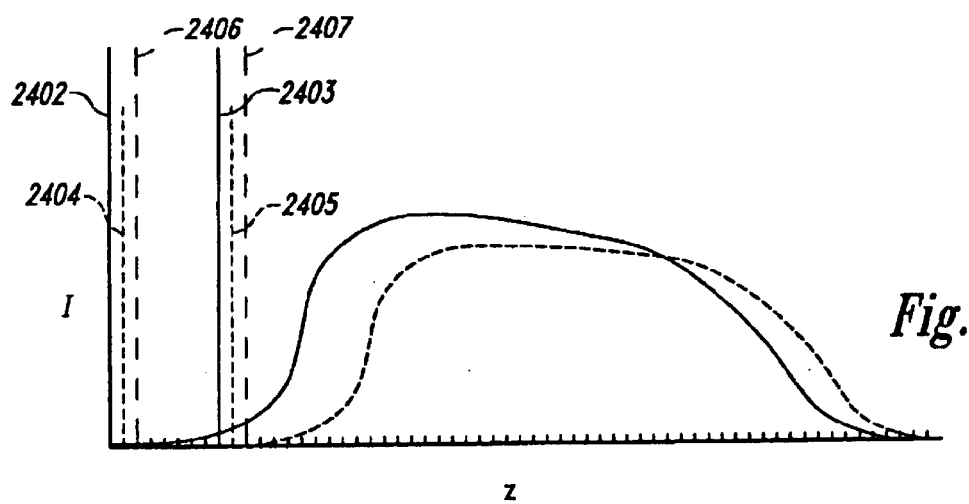

Next, window_focus divides the z-position range $Z_{max}^- - Z_{max}^-$ into a number of evenly sized increments. In one embodiment of the present invention, each increment represents a ¼ micron change in the z-position. The window_focus algorithm places the left edge of a window, or z-position interval, at each discrete z-position increment, with the last few increments near $Z_{max}^+$ omitted, as truncated windows would result. Therefore, there nearly as many windows as there are depth settings. FIG. 24 illustrates the windows initially constructed by window-focus. A first window is defined by vertical lines 2402–2403. A second window is defined by vertical dashed lines 2404–2405. A third window is defined by vertical dashed-and-crossed lines 2406–2407.

Figure 25:
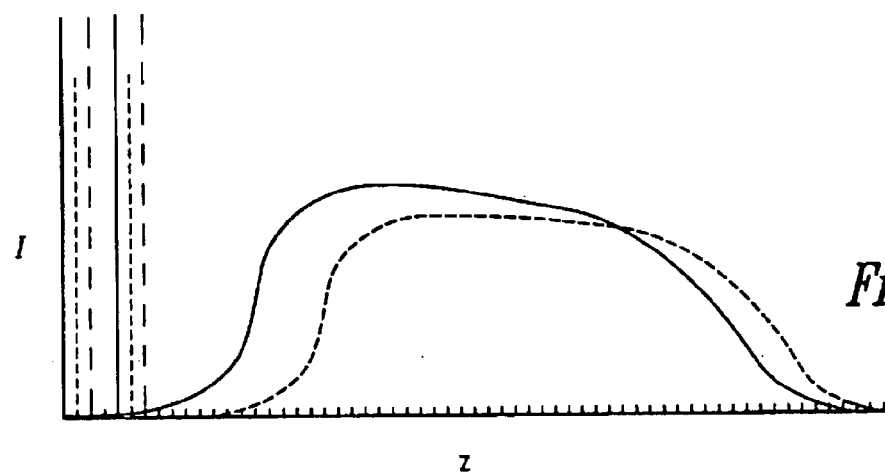
Figure 26:
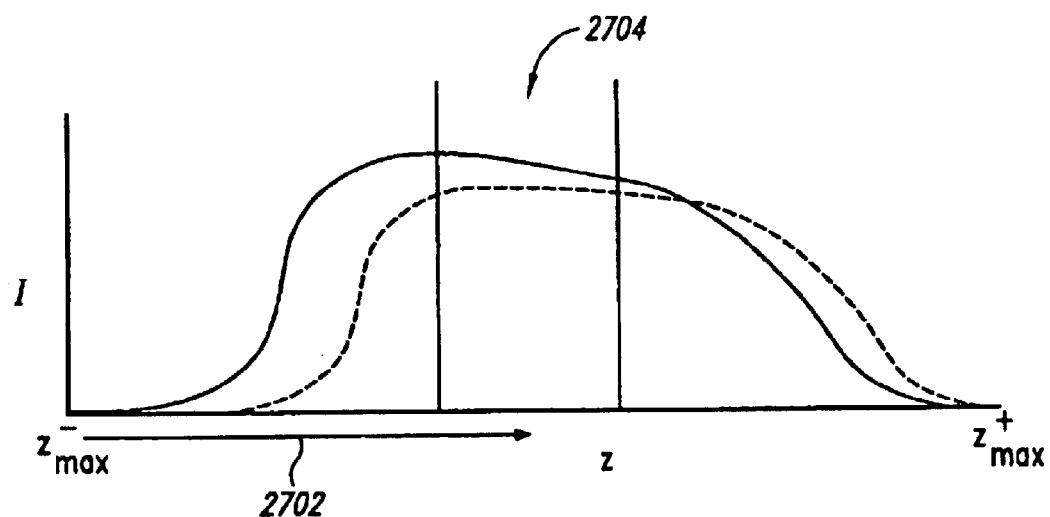
Figure 27:
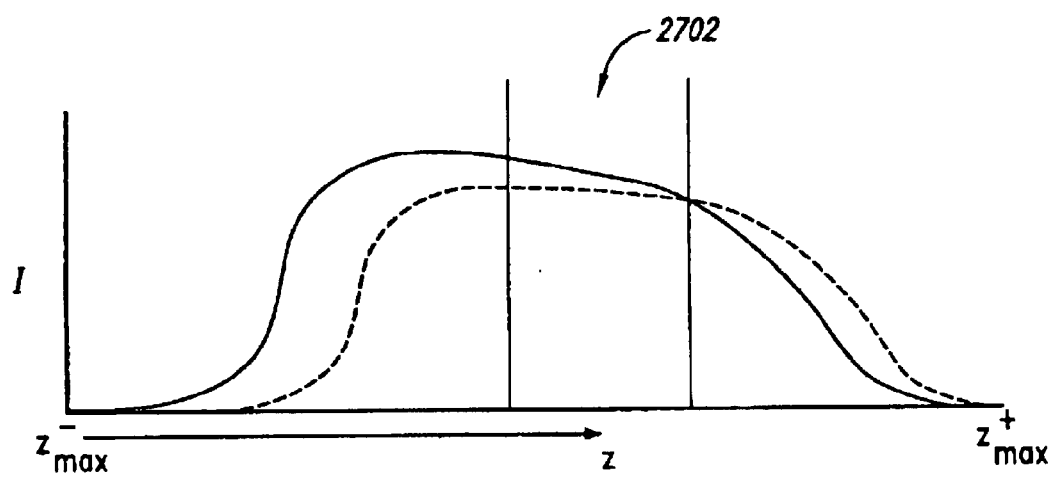

Initially, window_focus employs wider windows to determine approximate plateau intervals for each channel. In one embodiment, an initial 8 micron window is used. If the window-based plateau-interval determination fails to work for wider windows, it is tried again for narrower windows. FIG. 25 illustrates narrower windows. The plateau-interval determination is illustrated in FIGS. 26 and 27 for red and green channels, respectively. In FIG. 26, window_focus starts from the $Z_{max}^-$ z-position and proceeds rightward, as indicated by arrow 2602, determining a slope for each window. This slope can be calculated as the difference between the largest and smallest signal intensity seen inside the window expressed as a percentage of maximum intensity for the entire I/z curve between $Z_{max}^-$ and $Z_{max}^+$. Various methods can be used to determine the slope for a window, including applying a differential smoothing operator and then dividing the difference between the highest and lowest intensity values within the window by the length of the window increment. Alternative techniques may also be employed. Window_focus determines the slope of all initial windows. Window_focus looks for positions for which the difference between the maximum and minimum intensity values within the window are less than 2% of the maximum intensity found anywhere on the entire I/z curve. If window_focus finds at least one such window, it will return the z-position of the center of the window with the smallest intensity variation. If window_focus does not find a window with less than a 2% difference, then window_focus tries again with smaller-sized windows, in one embodiment, 6-micron windows If window_focus fails to find a window with less than a 2% difference, then window_focus tries again with 4 micron windows. If window_focus fails to find a 4-micron window with less than a 2% difference, then window_focus returns the 4-micron with the smallest intensity variations, using an RMS-like intensity variation measure discussed below. In FIG. 26, window 2704 is shown as meeting the criteria for a plateau window, although, as pointed out above, the slope of the plateau in the figures is exaggerated, and thus appears to create an intensity variation greater than 2%.

Figure 28A:
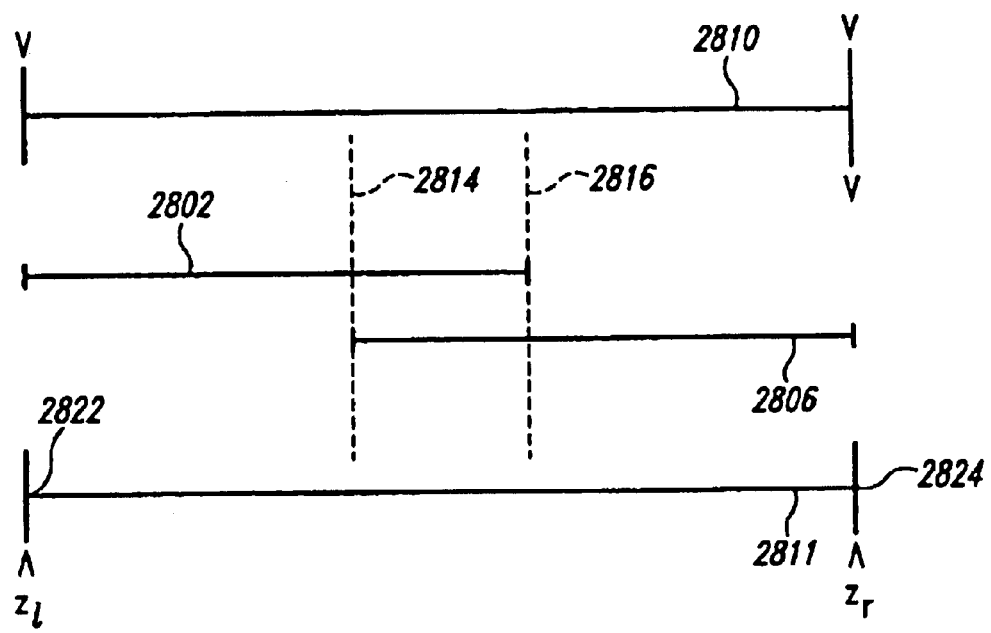
Figure 28B:
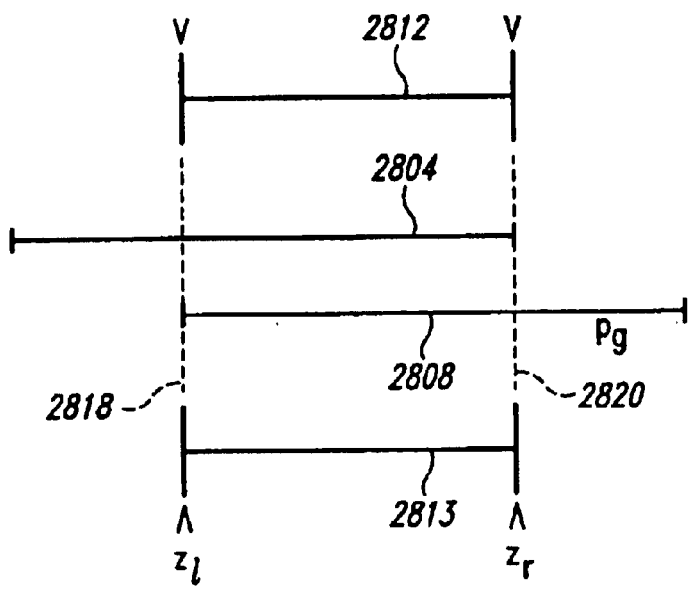
Figure 29:
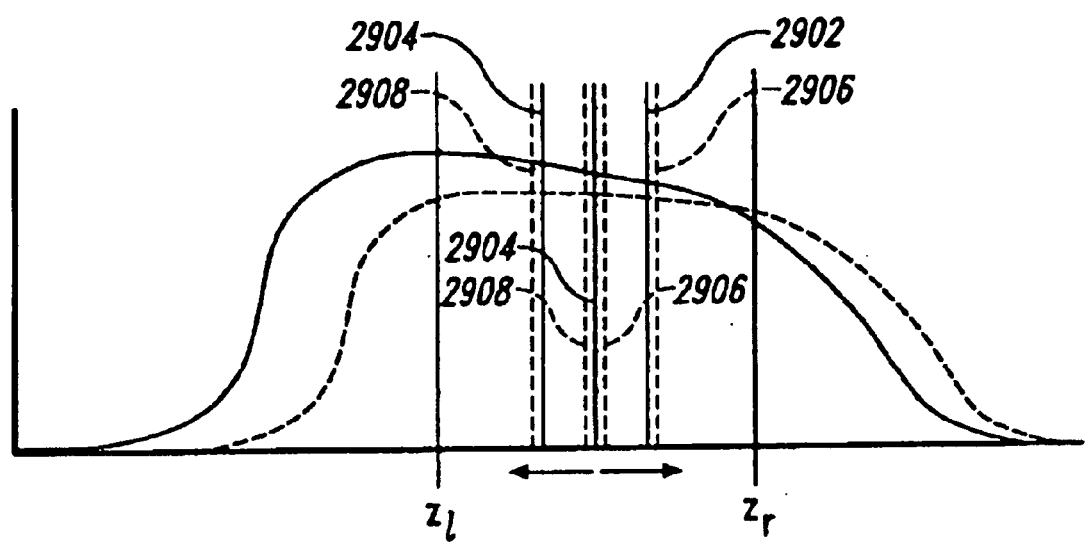

FIG. 27 illustrates determination of the plateau window 2702 for the green channel. Thus, by the window-based method, a red-channel plateau interval 2704 and a green-channel plateau interval 2702 are determined with respect to the z-position coordinate axis. As shown in FIGS. 28A–B, window_focus determines an overlap region common to the determined plateau intervals for each channel. In FIGS. 28A–B, the plateau windows for the red channel (2802 and 2804) are plotted horizontally in z-position (with respect to the plateau windows for the green channel (2806 and 2808). Z axis segments (2810–2813) are plotted above and below the plateau-window plots. In FIG. 28A, the overlap region begins at z-position 2814 and extends to z-position 2816. In FIG. 28B, the overlap region begins at z-position 2818 and extends to z-position 2820. When, as in FIG. 28A, the overlap region is less than some threshold value, in one embodiment four microns, or the signal intensities within the plateau intervals differ from one another by greater than some threshold amount, in one embodiment 2 percent, then, as shown in FIG. 28A, a left boundary $Z_l$ 2822 and a right boundary $Z_r$ 2824 are chosen as the left-most and right-most boundaries of the plateau intervals. By contrast, when the width of the overlap region exceeds a threshold value and the signal intensities within the plateau intervals differ by less than a threshold amount, then the left boundary $Z_l$ is chosen as the left-most point of the overlap 2818 and the right boundary $Z_r$ is chosen as the right-most point of the overlap region 2820, as shown in FIG. 28B.

Window_focus then centers smaller windows, in one embodiment, 2-micorn windows, at each z-position within the left and right boundaries, and searches, starting from the center, to find a small window with acceptable criteria most close to the center of the $Z_l$-to-$Z_r$ interval. The criteria used in one embodiment, for two-micron narrow windows, is that the signal intensities within the window must differ by less than 1 percent. In one embodiment, the search first considers narrow window 2902, next considers window 2904, next considers window 2906, next considers window 2908, and so forth, in a ping-pong like fashion. The first window considered that meets the criteria is selected as the focus window, and the z-position of the window's center is selected as the focus $Z_f$.

FIGS. 30 and 31 show flow-control diagrams for the routine "window_focus" and the routine "micro_focus," called from the routine "window_focus." Beginning with FIG. 30 in step 3002, window_focus receives the I/z data for scans of the reference array in each channel. In step 3004, window_focus determines the z-positions for the signal intensity peaks for each channel, as discussed above with reference to FIG. 23, and checks to see that they are within the central 80-percent interval of the full z-position range $Z_{max}^-$ to $Z_{max}^-$. If all the peak positions are not within the 80 percent central range, as determined by window_focus in step 3006, then an error is returned. Otherwise, in the nested for-loops comprising steps 3008–3014, window_focus determines the plateau intervals for each channel, as described above with reference to FIGS. 26–28B. Then, as discussed with reference to FIG. 29, window_focus calls the routine "micro_focus," in step 3024, to compute the z-position corresponding to the optimal focus distance $Z_f$, returning the optimal focus z-position $Z_f$ in step 3026, along with a status value indicating whether or not the plateau determination carried out in steps 3008–3014 successfully completed. Step 3008 is the first step of the outer for-loop of the nested for-loops of steps 3008–3014. The outer for-loop is repeated over a series of decreasing window sizes, as described with reference to FIGS. 24–25, in order to select plateau intervals for each channel scanned by the molecular array scanner.

The inner for-loop comprising steps 3009–3011 determines plateau intervals for each channel by the method described above with reference to FIGS. 26 and 17. A flow-control diagram for the routine "determine_plateau_interval," called from step 3010, is not provided, as the technique is thoroughly described, above, with reference to FIGS. 26 and 27. As noted there, plateau intervals span z-positions corresponding to the top of a mesa, and are identified as windows with essentially flat or nearly flat slopes that follow steeply sloped windows that contain the walls of the mesa.

When the plateau intervals for all channels have been determined for a current window size, window_focus determines, in step 3011, whether the signal variation, or differences, within each plateau interval is less than 2%. If not, then, in step 3012, window_focus determines whether or not the current window size is the smallest window size allowed for the outer for-loop. If not, then window_focus decrements the window size, in step 3013, and control returns to step 2009, where the inner for-loop is again executed. If the smallest window size has been tried, then window_focus returns, as the plateau window for each channel, the smallest windows with the least variation in signal intensity, using an RMS-like measure to be discussed below. Once the plateau intervals for each channel are found, then, in step 3016, window_focus computes the overlap between plateau intervals. If the overlap is acceptable, as determined in step 3018, then, as described with reference to FIG. 28B, above, window_focus sets the left and right boundaries $Z_l$ and $Z_r$ respectively, to the left and right boundaries of the overlap region, in step 3020. Otherwise, as described above with reference to FIG. 28A, window_focus sets the $Z_l$ and $Z_r$ boundary z-position values to the left-most z-position and right-most z-position of the various plateau intervals, in step 3022. Note that this step may also set an error return value to indicate an error condition corresponding to not finding a suitable plateau window for at least one channel. Following setting of the $Z_l$ and $Z_r$ boundary z-positions in step 3020 or 3022, window_focus calls the routine "micro_focus" instep 3018.

FIG. 31 shows a flow-control diagram for the routine "micro_focus," called from step 3018 of FIG. 30. In step 3102, micro_focus computes the center of the $Z_l$-to-$Z_r$ interval $Z_c$. Next, in step 3104, micro_focus applies the small windows to each increment within the $Z_l$-to-$Z_r$ interval, starting with the center of the $Z_l$-to-$Z_r$ interval $Z_c$. In one embodiment of the present invention, 2-micron windows are used. In step 3106, micro_focus determines whether there are an odd number of windows in the $Z_l$-to-$Z_r$ z-position range. If so, then in step 3108, micro_focus determines whether the center window has acceptable characteristics. As discussed above with reference to FIG. 29, acceptable characteristics may include a variation of signal intensities within the center window less than 1 percent. Alternatively, a slope-based method or another method for determining the degree of signal-intensity constancy within the window may be employed. If the center window is acceptable, then, in step 3110, micro_focus sets the z-position corresponding to the optimal focus distance, $Z_f$, to the z-position of the center of the center window and returns success. Otherwise, in the for-loop comprising steps 3112–3116, micro_focus carries out a ping-pong search of windows, out from the central z-position $Z_c$, to find an acceptable window closest to the center $Z_c$. The index i is set to the first window to the right of the center, and the index j is set to index the first window to the left of the center. In each iteration of the for-loop, the index i is incremented and the index j is decremented by 1 increment, in step 3116. In step 3113, micro_focus determines whether the window index by index i is acceptable, according to the criteria described above for acceptability of the center window in step 3108. If so, then control flows to step 3110, where the z-position corresponding to the optimal focus distance $Z_f$ is set to the center of the window indexed by variable i. Otherwise, if the window indexed by index j is acceptable according to the criteria applied to the central window in step 3108, then the z-position corresponding to the optimal focus distance $Z_f$ is set to the center of the window indexed by j, in step 3110. Otherwise, if there are more windows to consider in the range $Z_l$-to-$Z_r$, as determined in step 3115, then the indices are incremented and decremented in step 3116 and another iteration of the for-loop is carried out. If an acceptable window is not found following termination of the for-loop then, in step 3118, micro_focus computes a root-mean-square-like ("RMS-like") value, $$\sqrt{((\max(I_r) - \min(I_r))/I_{rmax})^2 + ((\max(I_g) - \min(I_r))/I_{gmax})^2},$$

for each window, where $\max(I_r)$ is maximum red-channel intensity for the window, $\min(I_r)$ is the minimum red-channel intensity for the window, $I_{rmax}$ is the maximum red intensity of the red-channel I/z function, $\max(I_g)$ is maximum green-channel intensity for the window, $\min(I_g)$ is the minimum green-channel intensity for the window, and $I_{gmax}$ is the maximum green intensity of the green-channel I/z function. Micro_focus then selects the window with the smallest RMS-like value in step 3120. The z-position of the center of the selected window is returned as the z-position corresponding to the optimal focus distance $Z_f$.

Although the present invention has been described in terms of a particular embodiment, it is not intended that the invention be limited to this embodiment. Modifications within the spirit of the invention will be apparent to those skilled in the art. For example, many different scan patterns may be used to construct the I/z data employed by the automated focus-distance determination routines. Different ranges of window sizes may be employed, and different orderings in window searching may be employed. The automated focus-distance determination routines can be implemented in many different languages, or hardware circuits, in an almost limitless number of ways, using different modular organizations and control logic. The methods was generally described in flow-control diagrams to include an arbitrary number of channels, and is intended to be applicable for 1-channel, 2-channel, and many-channel molecular array scanners.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. A method for determining an optimal focus distance of a molecular scanner, the method comprising:
   scanning portions of a reference array over a range of positions, each position representing a different distance between an illuminated region of the reference array and an emitted-light detection component of the molecular array, each portion scanned at a different position;
   assembling data collected from scanning the reference array into a representation of an intensity/position function; and
   employing a focus-distance determination method to determine an optimal focus distance or range of focus distances.

2. The method of claim 1 wherein scanning portions of a reference array over a range of positions relative to an emitted-light detection component further includes:
   for each position,
      scanning a set of rows,
      filtering the intensity values scanned for each row, and
      averaging the intensity values for the set of rows into an average intensity value for the position.

3. The method of claim 1 wherein assembling data collected from scanning the reference array into a representation of an intensity/position function further includes associating each position with an average intensity value.

4. The method of claim 1 wherein employing a focus-distance determination method to determine an optimal focus distance or range of focus distances further includes employing a peak-intensity-focus-distance determination method.

5. The method of claim 4 wherein the peak-intensity-focus-distance determination method comprises:
   using an intensity/position function for each channel of the molecular array scanner,
      determining the position of the peak intensity in the intensity/position function, and
      starting from the peak-intensity position, moving right and left in position in order to identify a left plateau position and a right plateau position at which the corresponding intensity falls below a threshold value, and selecting the positions between the left plateau position and the right plateau position as the plateau interval for the channel;
   determining an overlap position interval corresponding to the overlap in position of the plateau intervals of each channel; and
   when the overlap position interval and plateau for each channel meet acceptance criteria, returning a position within a plateau interval as the focus distance.

6. The method of claim 5 wherein the acceptance criteria comprise the overlap position interval having a size greater than an overlap position interval threshold size and the plateau for each channel having a size greater than a plateau threshold size.

7. The method of claim 1 wherein employing a focus-distance determination method to determine an optimal focus distance or range of focus distances further includes employing a window-focus-distance determination method.

8. The method of claim 7 wherein the focus-distance determination method comprises:
   using an intensity/position function for each channel of the molecular array scanner,
      determining the position of the peak intensity in the intensity/position function for each channel, and
      returning an error when the positions of peak intensity for each channel do not all fall within a central portion of the range of position;
   finding, for each channel, a plateau interval in the intensity/position function for the channel;
   finding an overlap position interval that represents overlap in positions from the plateau intervals for each channel;
   when the overlap position interval meets a set of acceptance criteria,
      finding a focus-distance within the overlap position interval.

9. The method of claim 8 wherein finding, for each channel, a plateau interval in the intensity/position function for the channel further includes:
   for decreasing window intervals sizes,
      searching window intervals in the position range of the intensity/position function for the channel for a window interval in which intensities differ by less than a threshold value,
      when a single window interval contains intensities that differ by less than the threshold value, returning the single window interval,
      when more than one window interval contains intensities that differ by less than a threshold value, selecting a window interval having the least difference in intensities and returning the selected window interval, and
      when the current window interval size is less than a minimum window interval size, returning a default window interval.

10. The method of claim 9 wherein finding a focus-distance within the overlap position interval further includes:
   starting from a center position within the overlap position interval, searching outward from the center position to find a small window interval closest to the center position with intensity differences less than a small-window-final-intensity-difference threshold.

11. Signal intensity data scanned from the surface of a molecular array at a focus distance determined by the method of claim 1 encoded by:
   storing representations of the signal intensity data in a machine readable medium;
   transmitting representations of the signal intensity data over an electronic communications medium;
   displaying the signal intensity data on a display device; and
   printing representations of the signal intensity data in a human readable medium.

12. A set of computer instructions for carrying out the method of claim 1 encoded by one of:

storing the computer instructions in a machine readable medium;

transmitting the computer instructions over an electronic communications medium; and printing the computer instructions in a human readable medium.

13. A molecular array scanner comprising:

a probe-molecule excitation system;

an emitted-light photodetection system that produces a signal representative of the emitted-light intensity;

a molecular-array-holding stage that holds a molecular array for scanning and that can be moved through a range of positions that place an illuminated region of the surface of the molecular array at different distances from the emitted-light photodetection system; and an automated focus-distance-determination subsystem that scans portions of a reference array over a range of positions, each position representing a different distance between an illuminated region of the reference array and the emitted-light photodetection system, each portion scanned at a different position;

assembles data collected from the scan of the reference array into a representation of an intensity/position function; and employs a focus-distance determination method to determine an optimal focus distance or range of focus distances based on the representation of the intensity/position function.

14. The molecular array scanner of claim 13 wherein the automated focus-distance-determination subsystem scans portions of a reference array over a range of positions by:

for each position,
scanning a set of rows,
filtering the intensity values scanned for each row, and
averaging the intensity values for the set of rows into an average intensity value for the position.

15. The molecular array scanner of claim 14 wherein the automated focus-distance-determination subsystem assembles data collected from scanning the reference array into a representation of an intensity/position function by associating each position with an average intensity value.

16. The molecular array scanner of claim 14 wherein the automated focus-distance-determination subsystem employs a focus-distance determination method to determine an optimal focus distance or range of focus distances by employing a peak-intensity-focus-distance determination method.

17. The molecular array scanner of claim 14 wherein the automated focus-distance-determination subsystem employs a focus-distance determination method to determine an optimal focus distance or range of focus distances by employing a window-focus-distance determination method.

18. Signal intensity data scanned from the surface of a molecular array at a focus distance determined by the molecular array scanner of claim 13 encoded by:

storing representations of the signal intensity data in a machine readable medium;

transmitting representation of the signal intensity data over an electronic communications medium;

displaying the signal intensity data on display device; and printing representations of the signal intensity data in a human readable medium.

19. A set of computer instructions that implement the molecular-array-scanner automated focus-distance-determination subsystem of claim 13 encoded by one of:

storing the computer instructions in a machine readable medium;

transmitting the computer instructions over an electronic communications medium; and printing the computer instructions in a human readable medium.

* * * * *